(12) United States Patent
Yu et al.

(10) Patent No.: US 11,717,575 B2
(45) Date of Patent: Aug. 8, 2023

(54) ONE-POT PROCESS FOR PREPARING INTERMEDIATE OF ANTIBODY-DRUG CONJUGATE

(71) Applicant: MABPLEX INTERNATIONAL CO., LTD., Shandong (CN)

(72) Inventors: Zhaoxing Yu, Shandong (CN); Xinfang Li, Shandong (CN); Mingchao Lan, Shandong (CN); Xinjie Mao, Shandong (CN)

(73) Assignee: MABPLEX INTERNATIONAL CO., LTD., Shandong (CN)

( * ) Notice: Subject to any disclaimer, the term of this patent is extended or adjusted under 35 U.S.C. 154(b) by 110 days.

(21) Appl. No.: 15/733,309

(22) PCT Filed: Feb. 13, 2020

(86) PCT No.: PCT/CN2020/074987
§ 371 (c)(1),
(2) Date: Jun. 23, 2020

(87) PCT Pub. No.: WO2020/233174
PCT Pub. Date: Nov. 26, 2020

(65) Prior Publication Data
US 2021/0085799 A1 Mar. 25, 2021

(30) Foreign Application Priority Data

May 20, 2019 (CN) .................. 201910420868.X
Sep. 26, 2019 (CN) .................. 201910916198.0
(Continued)

(51) Int. Cl.
*A61K 47/68* (2017.01)
*A61K 47/65* (2017.01)
*A61K 45/06* (2006.01)

(52) U.S. Cl.
CPC .......... *A61K 47/6801* (2017.08); *A61K 47/65* (2017.08); *A61K 45/06* (2013.01)

(58) Field of Classification Search
None
See application file for complete search history.

(56) References Cited

U.S. PATENT DOCUMENTS

| 2016/0015832 A1 | 1/2016 | An et al. |
| 2017/0202974 A1 | 7/2017 | Li et al. |

(Continued)

FOREIGN PATENT DOCUMENTS

| CA | 3039559 | | 4/2018 |
| CN | 103933575 | * | 7/2014 |

(Continued)

OTHER PUBLICATIONS

Dubowchik et al., Bioconjugate Chem. 2002, 13, 855-869 (Year: 2002).*

(Continued)

*Primary Examiner* — Karl J Puttlitz
(74) *Attorney, Agent, or Firm* — Parker Highlander PLLC

(57) ABSTRACT

The present invention relates to a "one-pot process" for preparing intermediate of antibody-drug conjugate. The preparation process provided by the present invention is simple in operation, and needs no such steps like concentration, washing and filtration of the intermediate reaction liquid, disposal of the organic waste liquid, and packaging and storage of the intermediate. The entire reaction system comprises only one separation and purification treatment, saving costs for labor, equipment, venues, raw materials, etc., and greatly reducing the pollution to the environment. In addition, the "one-pot process" for preparing intermediate of antibody-drug conjugate of the present invention produces the intermediate of antibody-drug conjugate with (Continued)

higher yield. The "one-pot process" for preparing intermediate of antibody-drug conjugate provided by the present invention is more suitable for scale-up production.

5 Claims, 1 Drawing Sheet

(30) Foreign Application Priority Data

| Sep. 26, 2019 | (CN) | 201910916200.4 |
| Sep. 26, 2019 | (CN) | 201910916242.8 |
| Sep. 26, 2019 | (CN) | 201910916470.5 |
| Sep. 26, 2019 | (CN) | 201910916508.9 |
| Sep. 26, 2019 | (CN) | 201910916510.6 |

(56) References Cited

U.S. PATENT DOCUMENTS

| 2018/0055948 A1 | 5/2018 | Huang et al. |
| 2020/0138968 A1 | 5/2020 | Huang et al. |

FOREIGN PATENT DOCUMENTS

| CN | 107427591 | * | 12/2017 |
| CN | 107921030 | * | 4/2018 |
| CN | 108727498 |   | 11/2018 |
| CN | 108727499 | * | 11/2018 |
| CN | 109200291 |   | 1/2019 |
| CN | 110507824 |   | 11/2019 |
| JP | 2018-505740 |   | 3/2018 |
| WO | 2007008603 | * | 1/2007 |
| WO | WO 2007/008603 |   | 1/2007 |
| WO | WO 2014/191578 |   | 12/2014 |
| WO | WO 2016/008112 |   | 1/2016 |
| WO | WO 2016/088112 |   | 6/2016 |
| WO | WO2016128983 A1 |   | 8/2016 |
| WO | WO 2017/214282 |   | 12/2017 |
| WO | WO2018031662 A1 |   | 2/2018 |
| WO | WO 2018/064964 |   | 4/2018 |
| WO | WO 2019/034177 |   | 2/2019 |
| WO | WO 2019/108797 |   | 6/2019 |
| WO | WO 2019/223579 |   | 11/2019 |
| WO | WO 2019/223653 |   | 11/2019 |

OTHER PUBLICATIONS

Hayashi et al., Chem. Sci., 2016, 7, 866-880 (Year: 2016).*
Extended European Search Report issued in European Patent Application No. 20733678.5, dated Jul. 9, 2021.
Office Communication issued in Canadian Patent Application No. 3,085,001, dated Dec. 15, 2020.
Office Communication issued in Australian Patent Application No. 2020204250, dated Oct. 9, 2020.
Office Action issued in Japanese Application No. 2020-535962, dated Jan. 4, 2022, and English language translation thereof.

* cited by examiner

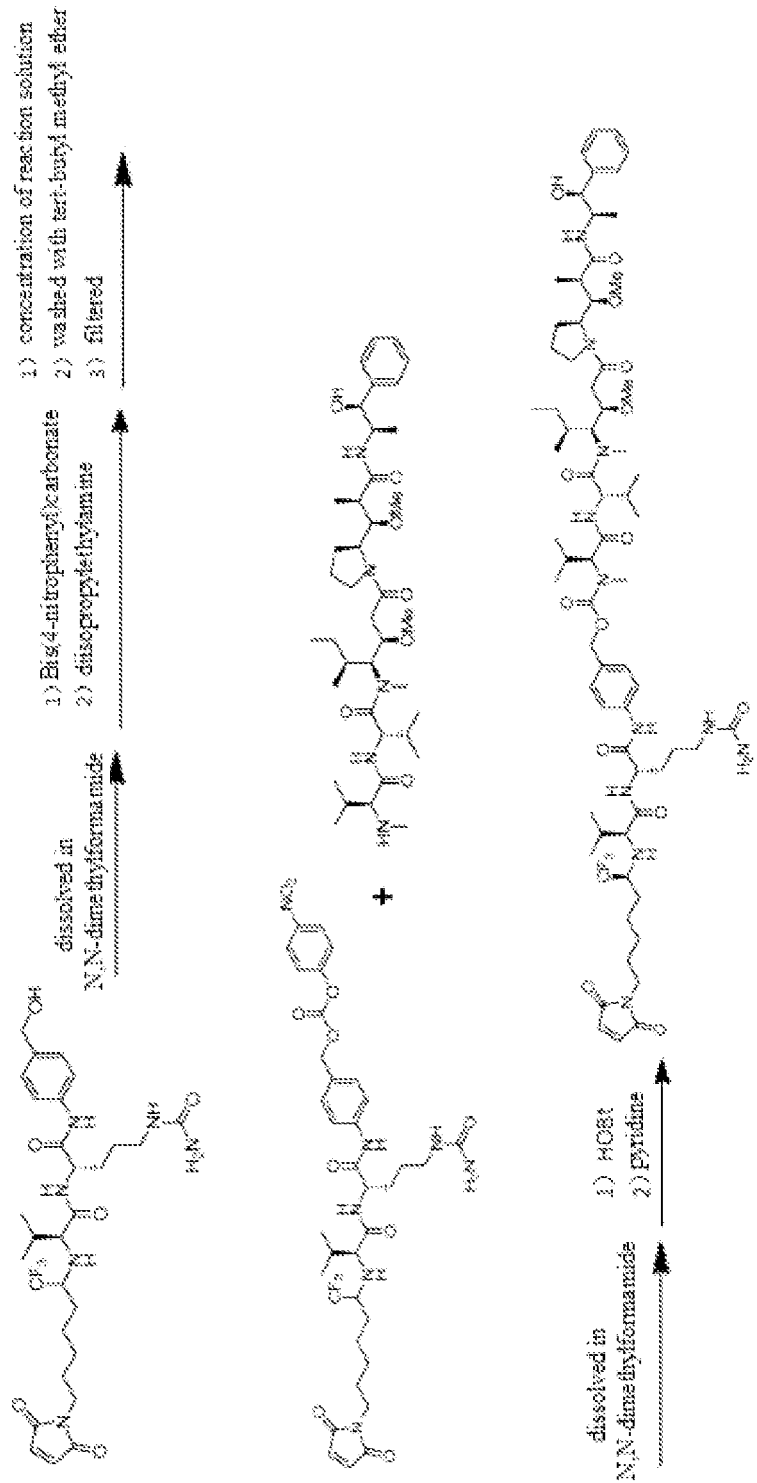

ONE-POT PROCESS FOR PREPARING INTERMEDIATE OF ANTIBODY-DRUG CONJUGATE

This application is a national phase application under 35 U.S.C. § 371 of International Application No. PCT/CN2020/074987, filed Feb. 13, 2020, which claims the benefit of Chinese Patent Application Nos. 201910420868.X, filed May 20, 2019, No. 201910916198.0, filed Sep. 26, 2019, No. 201910916200.4, filed Sep. 26, 2019, No. 201910916242.8, filed Sep. 26, 2019, No. 201910916470.5, filed Sep. 26, 2019 and No. 201910916508.9, filed Sep. 26, 2019 and No. 201910916510.6, filed Sep. 26, 2019, the entirety of each of which is incorporated herein by reference.

FIELD

The present invention relates to the field of antibody-drug conjugates, in particular to a one-pot process for preparing intermediate of antibody-drug conjugate (i.e., linker portion-drug portion conjugate).

BACKGROUND

Antibody-drug conjugate (ADC) is a class of anti-tumor drugs comprising three portions: an antibody portion, a linker portion and a drug portion, in which the antibody portion and the drug portion are connected by the linker portion. The mechanism of action is to deliver the drug by virtue of the targeting ability of the antibody to the target cells (such as tumor cells) and then release the drug to kill the tumor cells.

At present, the most common method for synthesizing antibody-drug conjugates is to covalently link the linker portion and the drug portion in the liquid phase to form a linker-drug conjugate, and then perform thiol or amino coupling with the antibody to form the antibody-drug conjugate. Chinese Patent Publication No. CN107427591A details a general method for synthesis of linker-drug conjugates (see page 34 and pages 47-48 of the specification) (as shown in FIG. 1). The above general synthesis method comprises: in the first step, dissolving the linker containing free benzyl alcohol group in an appropriate solvent, adding bis(4-nitrophenyl)carbonate and diisopropylethylamine to the reaction system, and after several hours of reaction, extracting and purifying the intermediate product; and in the second step, dissolving the above intermediate product and the drug portion containing free amino groups in an appropriate solvent, adding 1-hydroxybenzotriazole and pyridine, and after several hours of reaction, removing the solvent under reduced pressure to obtain the linker-drug conjugate.

In the above two-step reaction system, the intermediates need to be extracted and purified, which will affect the final reaction yield. In addition, the above-mentioned preparation process has the inevitable defect of multi-system reaction during production, that is, the need for the concentration, washing and filtration of the reaction liquid in multiple steps, the disposal of the organic waste liquid, and the packaging and storage of the intermediates in the first step, which not only increases the production cost for consumables, labor, equipment, venues, etc., but also generates more waste liquid, increasing the overall production cost and production time.

Chinese Patent Application Publication No. CN107921030A also discloses a variety of linkers capable of covalently connecting to the antibody in a bridging coupling manner. It discloses an intermediate of antibody-drug conjugate (Py-MAA-Val-Cit-PAB-MMAE) (wherein, Py is 1,3,5-triacryloylhexahydro-1,3,5-triazine, CAS 959-52-4, available from Bailingwei Technology Co., Ltd. and Nanjing Kangmanlin Chemical Industry Co., Ltd.).

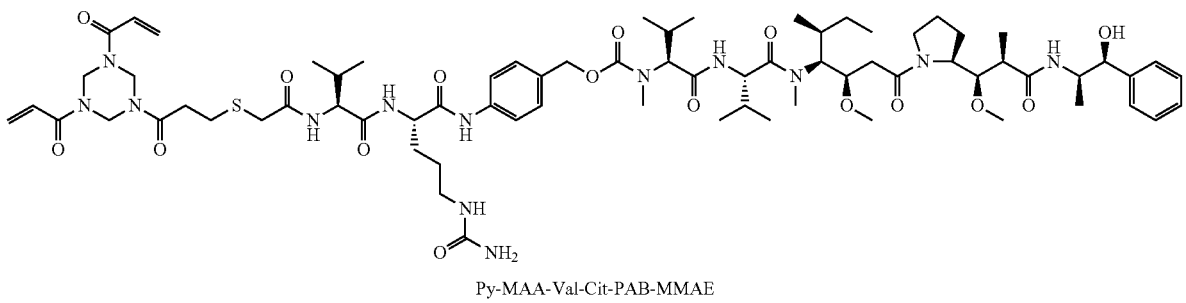 [SMILES: C=CC(=O)N1CN(C(=O)C=C)CN(C(=O)CCSCC(=O)N[C@H](C(=O)N[C@@H](CCCNC(N)=O)C(=O)Nc2ccc(COC(=O)N(C)[C@H](C(=O)N[C@H](C(=O)N(C)[C@@H]([C@@H](C)CC)[C@@H](CC(=O)N3CCC[C@H]3[C@H](OC)[C@@H](C)C(=O)N[C@H](C)[C@@H](O)c3ccccc3)OC)C(C)C)C(C)C)cc2)C(C)C)C1]

Py-MAA-Val-Cit-PAB-MMAE

In addition, the patent application also discloses a process for preparing an intermediate of antibody-drug conjugate (Py-MAA-Val-Cit-PAB-MMAD), in which the drug portion is MMAD (Demethyldolastatin 10):

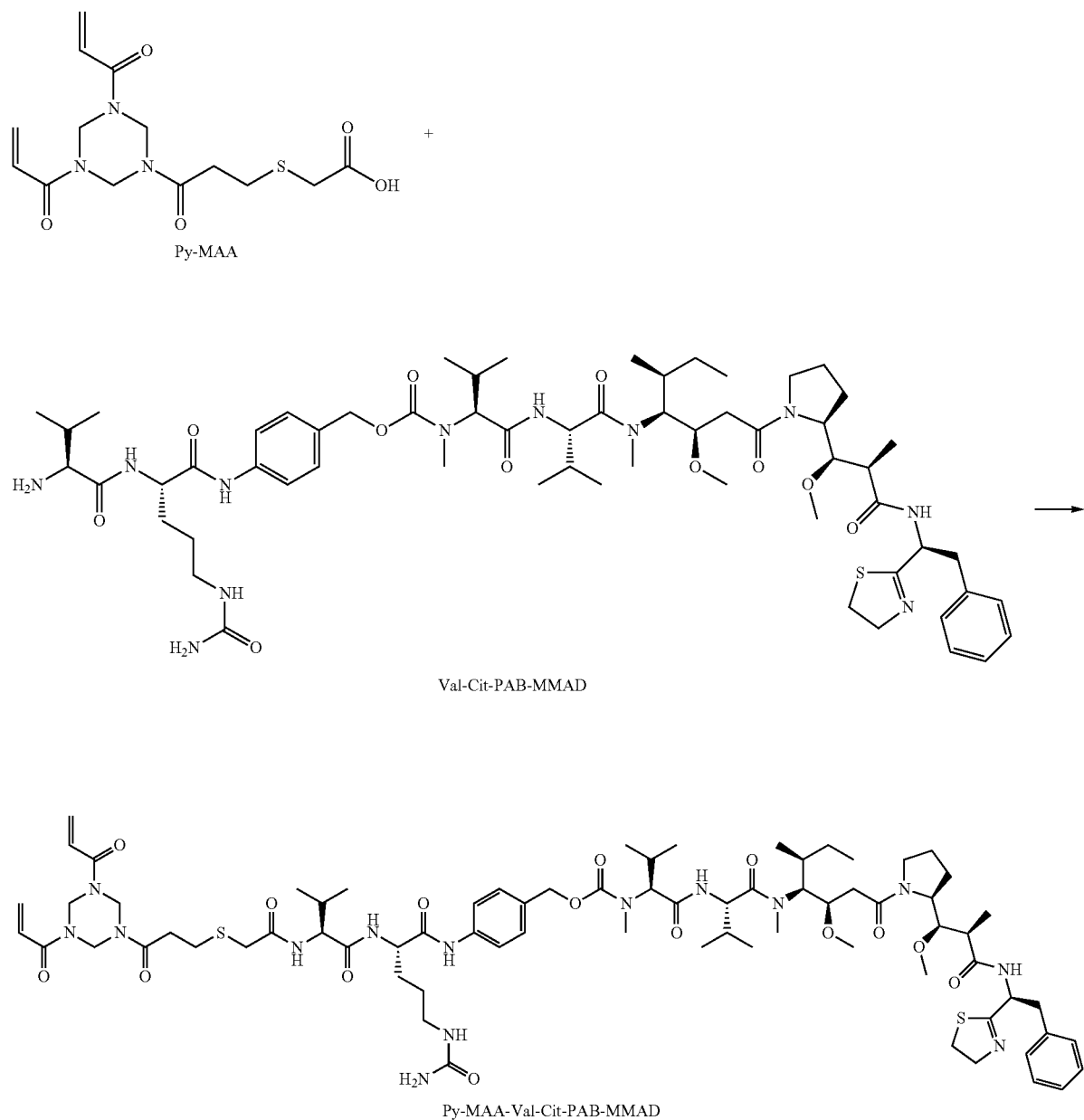

In this process, Val-Cit-PAB and the drug portion (MMAD) are first coupled together to form Val-Cit-PAB-MMAD conjugate, and then the product obtained after purification is reacted with Py-MAA to generate the intermediate of antibody-drug conjugate Py-MAA-Val-Cit-PAB-MMAD. This process also adopts multi-system synthesis. In addition, since the drug portion (such as MMAD/MMAE or MMAF, etc.) connected in the antibody-drug conjugate participates in the connection reaction in the early stage of the reaction (MMAD is added to the reaction system as a reactant when forming Val-Cit-PAB-MMAD), rather than the last step, the consumption of the drug portion (such as MMAD/MMAE or MMAF, etc.) used in the above process is huge, and since the drug portions (such as MMAD/MMAE or MMAF, etc.) connected in the antibody-drug conjugate are usually relatively expensive, the production cost is greatly increased.

SUMMARY

In order to solve the above problems, the present invention provides a "one-pot process" for preparing an intermediate of an antibody-drug conjugate (i.e., linker-drug conjugate).

Specifically, the present invention provides a process for preparing an intermediate of antibody-drug conjugate comprising a linker portion and a drug portion, wherein the intermediate of antibody-drug conjugate is Py-MAA-Val-Cit-PAB-D or MC-Val-Cit-PAB-D, wherein Py-MAA-Val-Cit-PAB or MC-Val-Cit-PAB in the intermediate is the linker portion, and D in the intermediate represents the linked drug portion comprising free amino groups, wherein the process comprises the following reaction route:

5                                    6
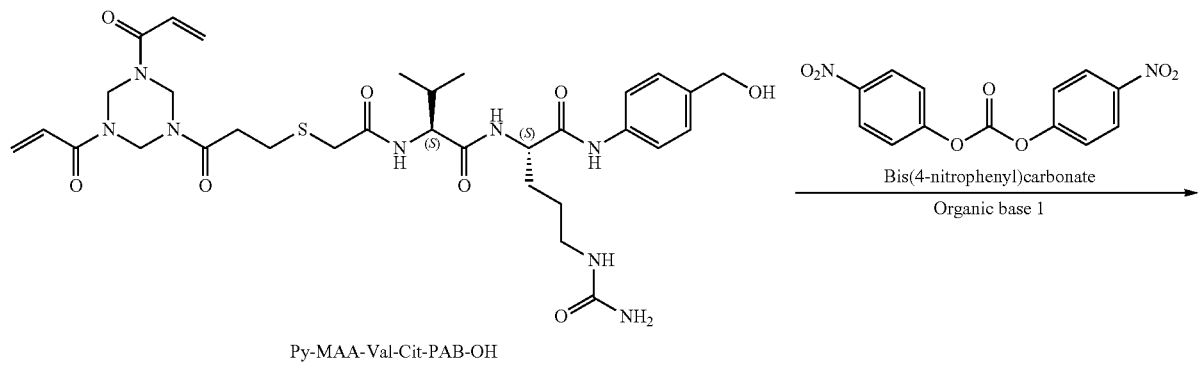
Py-MAA-Val-Cit-PAB-OH          Bis(4-nitrophenyl)carbonate
                                Organic base 1
                                →
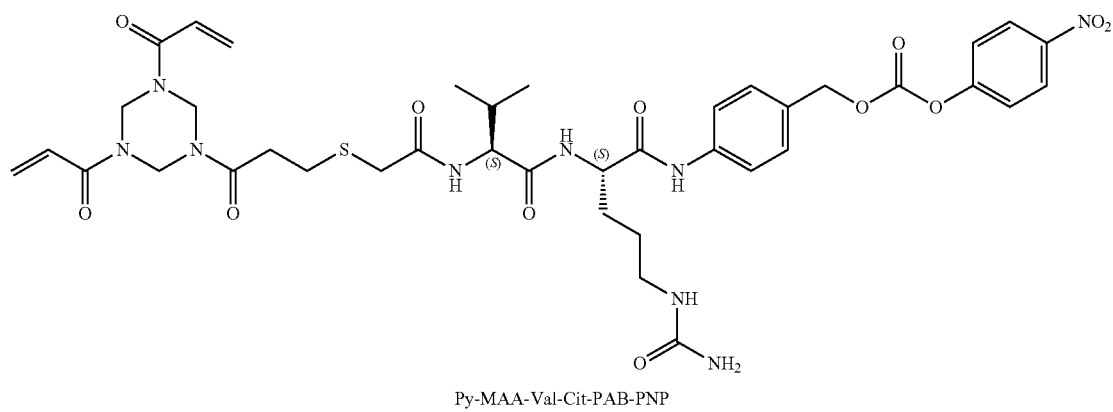
Py-MAA-Val-Cit-PAB-PNP
Drug portion D | i) Triazole catalyst
               | ii) Organic base 2
↓
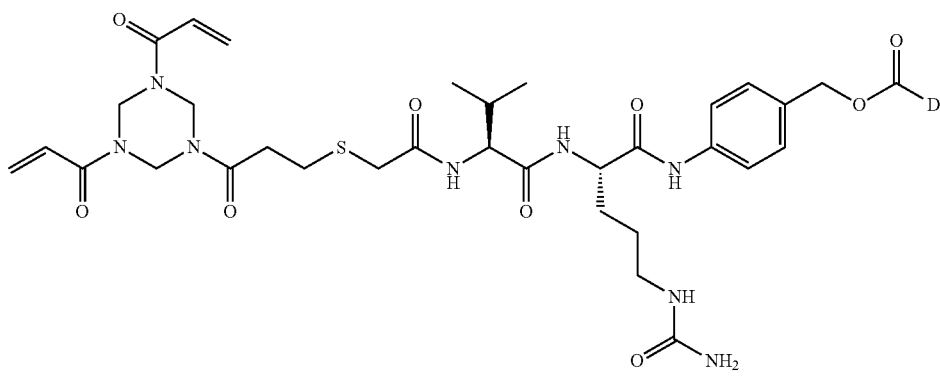
Py-MAA-Val-Cit-PAB-D                                       or
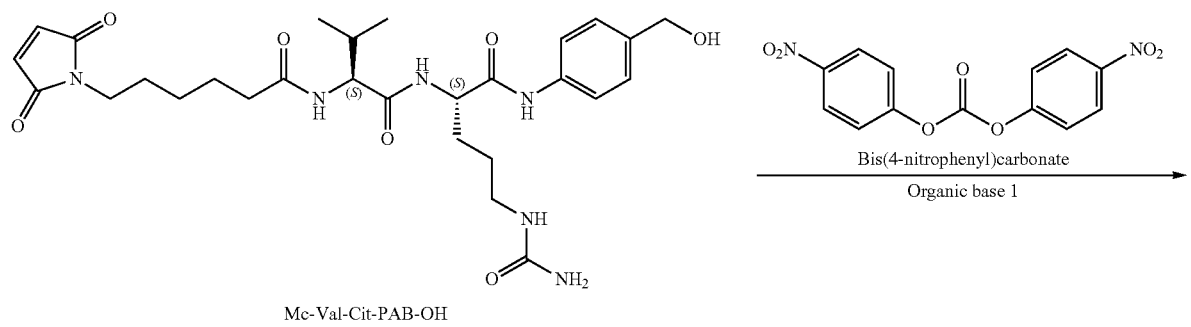
Mc-Val-Cit-PAB-OH          Bis(4-nitrophenyl)carbonate
                            Organic base 1
                            →

-continued

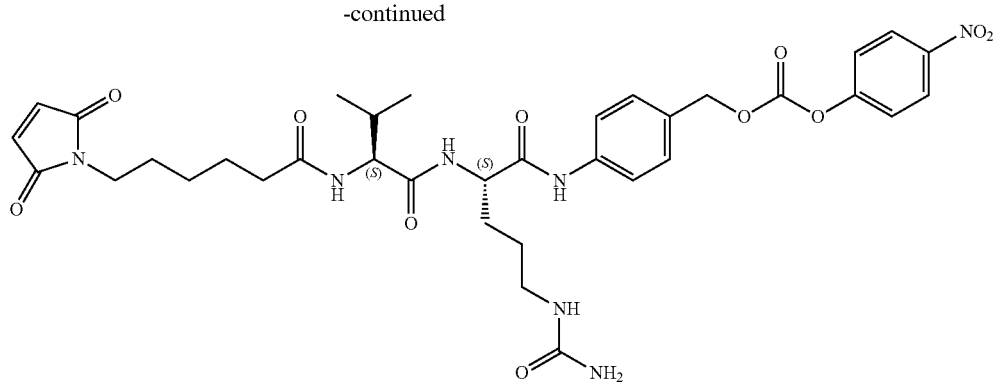

Mc-Val-Cit-PAB-PNP

Drug portion D  i) Triazole catalyst
ii) Organic base 2

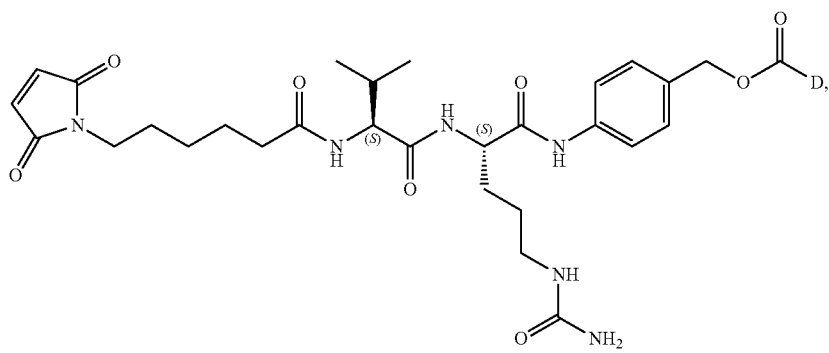

Mc-Val-Cit-PAB-D wherein the preparation process is a one-pot process in which two steps are carried out in one system.

Further, the process comprising reacting Py-MAA-Val-Cit-PAB-OH or MC-Val-Cit-PAB-OH with bis(4-nitrophenyl)carbonate (NPC) in the presence of an organic base, and after the completion of the reaction, further adding organic base, and then 1-hydroxybenzotriazole and the drug portion D into the same reaction system directly for further reaction.

Further, the drug portion D is auristatin cytotoxic agent, anthramycin cytotoxic agent, anthracycline cytotoxic agents or puromycin cytotoxic agent, or camptothecin analogs.

Further, the auristatin cytotoxic agent is MMAE, MMAF, MMAD or derivatives thereof; the anthramycin cytotoxic agent is anthramycin or derivative thereof; the anthracycline cytotoxic agent is daunorubicin, doxorubicin, epirubicin, idarubicin, mitoxantrone or derivatives thereof; the puromycin cytotoxic agent is puromycin or derivative thereof; and the camptothecin analogue is DX8951 (Exatecan) or derivative thereof.

Further, Py-MAA-Val-Cit-PAB-D or MC-Val-Cit-PAB-D has a structure as shown in the following formulas (1-22):

(1)

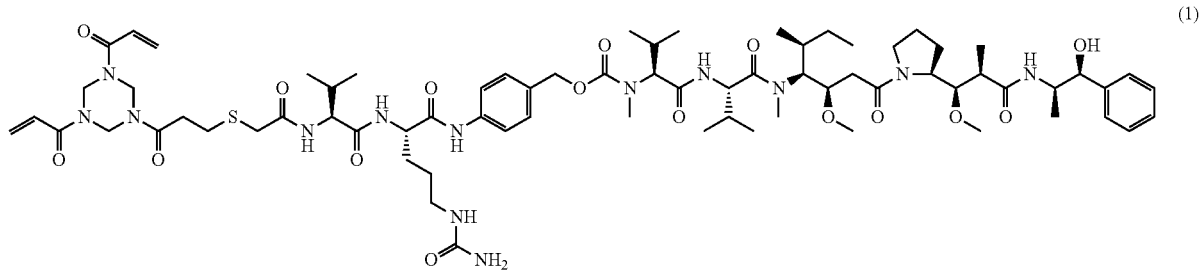

Py-MAA-Val-Cit-PAB-MMAE

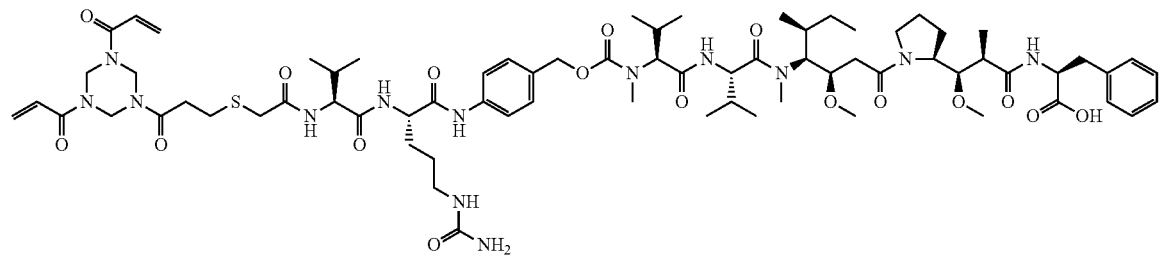
Py-MAA-Val-Cit-PAB-MMAF     (2)
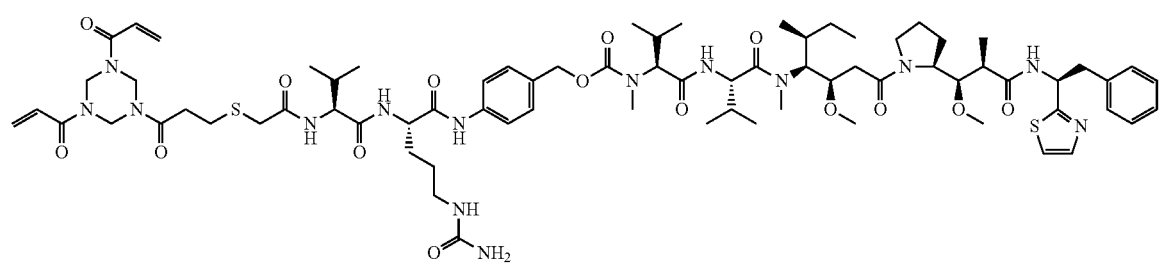
Py-MAA-Val-Cit-PAB-MMAD     (3)
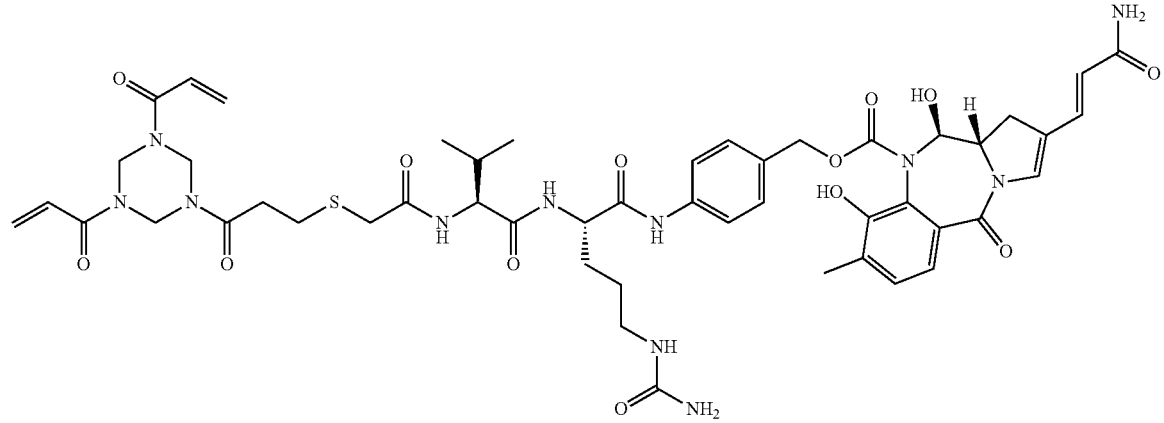
Py-MAA-Val-Cit-PAB-anthramycin     (4)
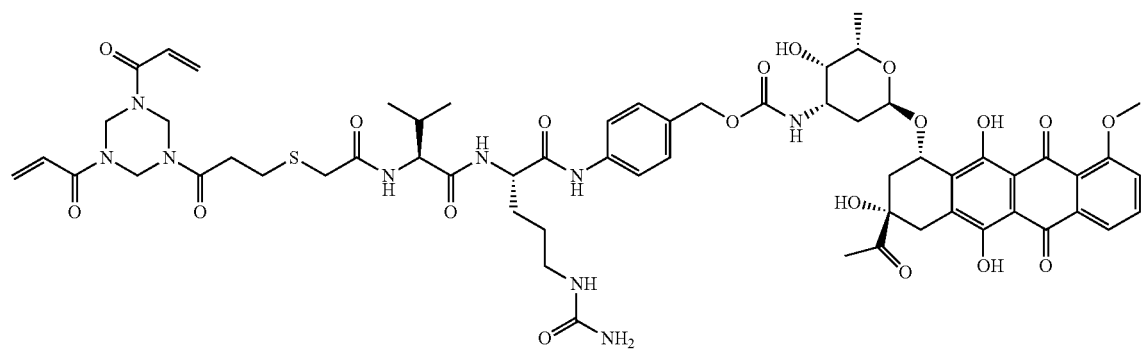
Py-MAA-Val-Cit-PAB-daunorubicin     (5)

-continued
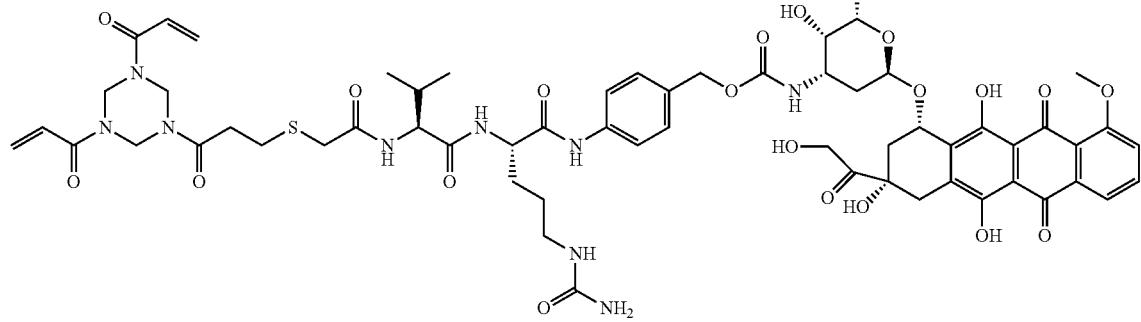
Py-MAA-Val-Cit-PAB-doxorubicin
(6)
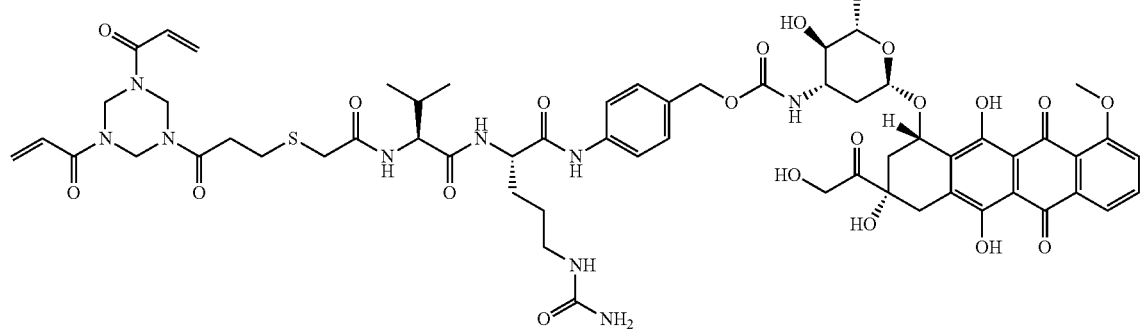
Py-MAA-Val-Cit-PAB-epirubicin
(7)
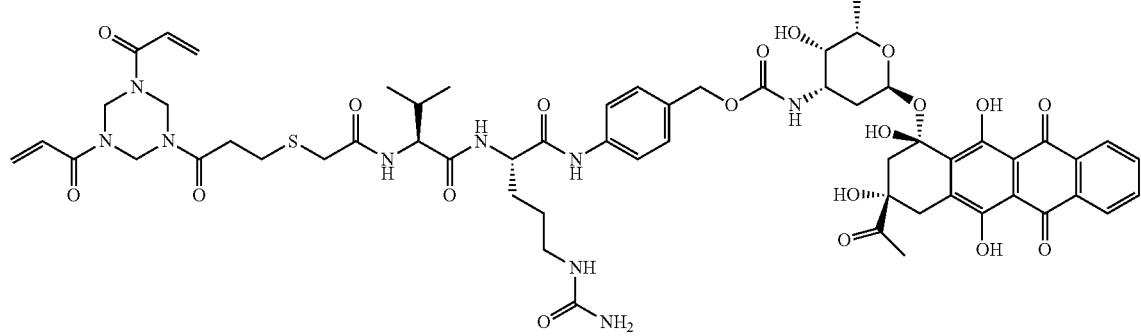
Py-MAA-Val-Cit-PAB-idarubicin
(8)

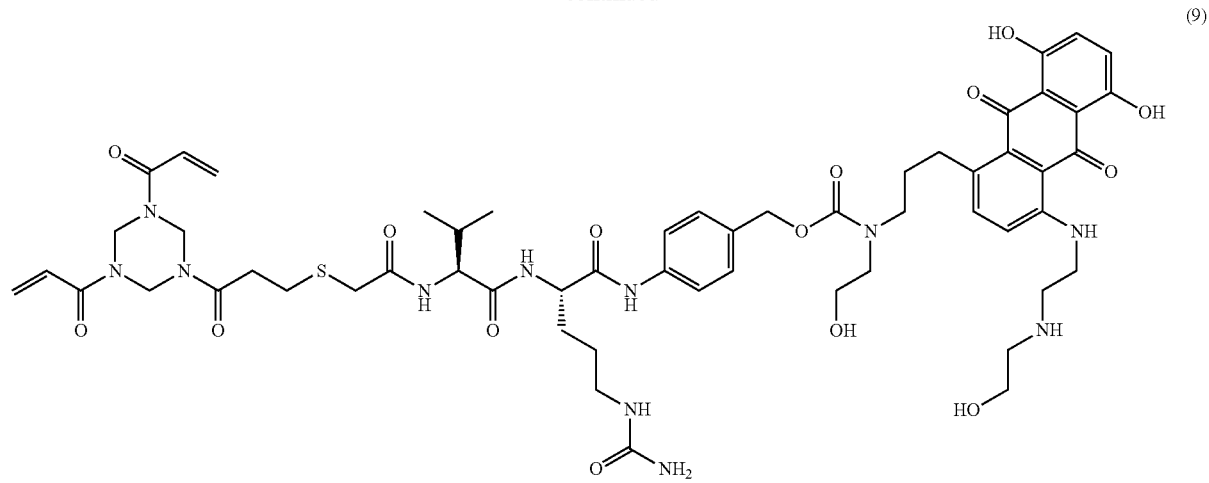
Py-MAA-Val-Cit-PAB-mitoxantrone
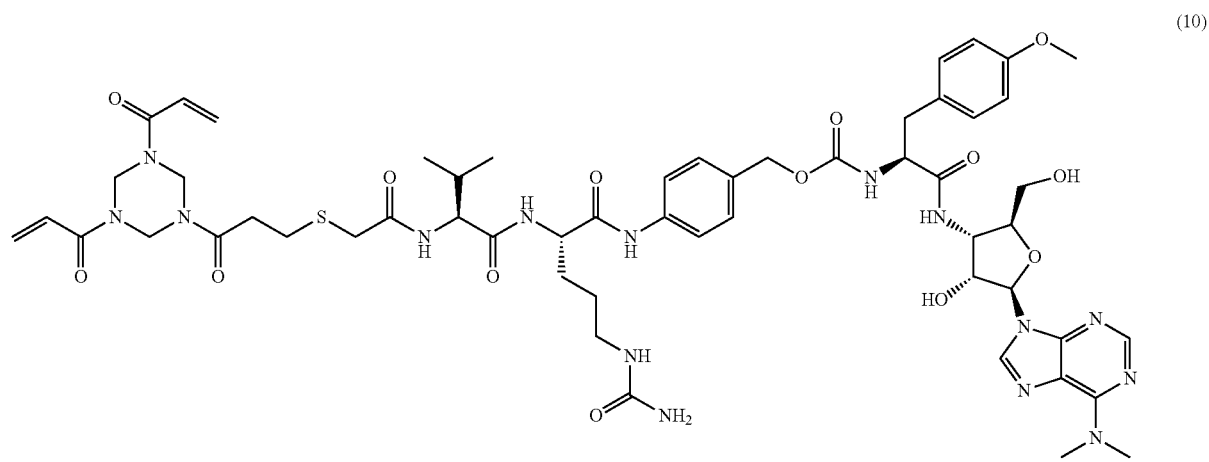
Py-MAA-Val-Cit-PAB-puromycin
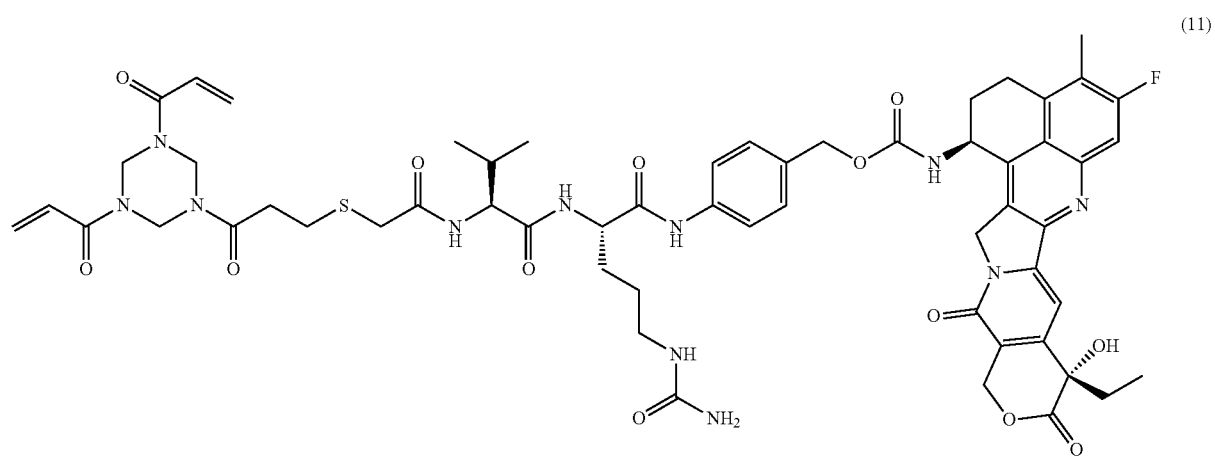
Py-MAA-Val-Cit-PAB-DX8951

(12)
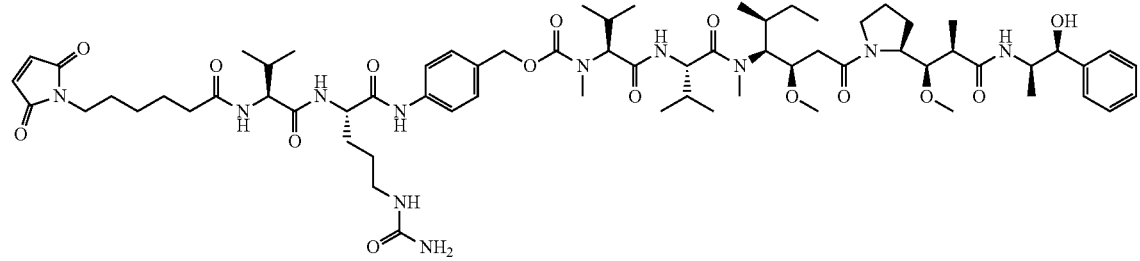
MC-Val-Cit-PAB-MMAE
(13)
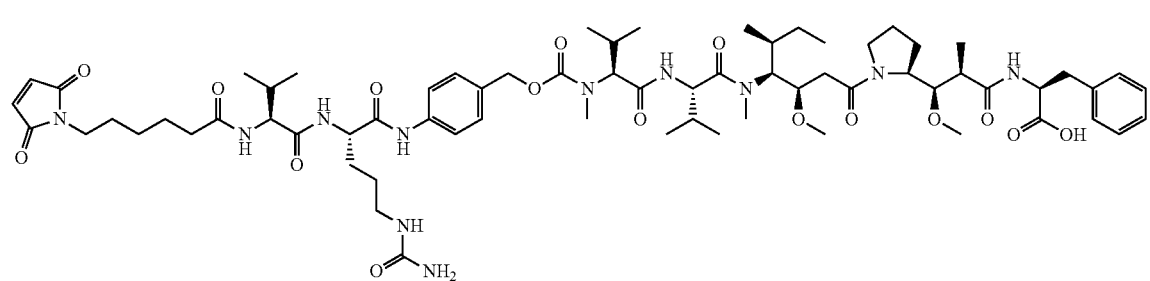
MC-Val-Cit-PAB-MMAF
(14)
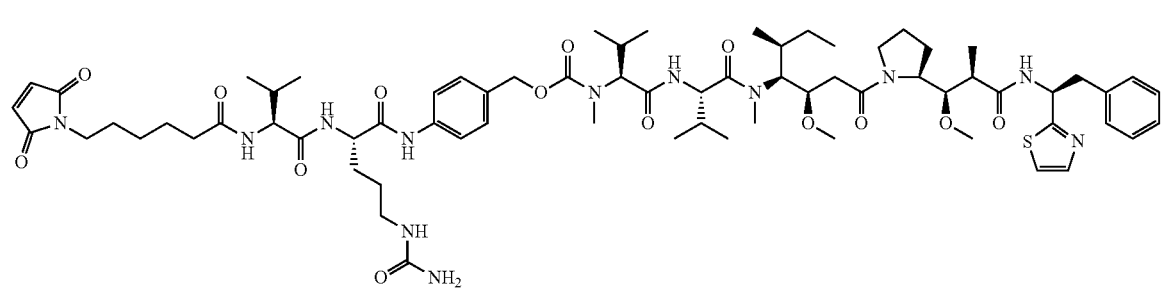
MC-Val-Cit-PAB-MMAD
(15)
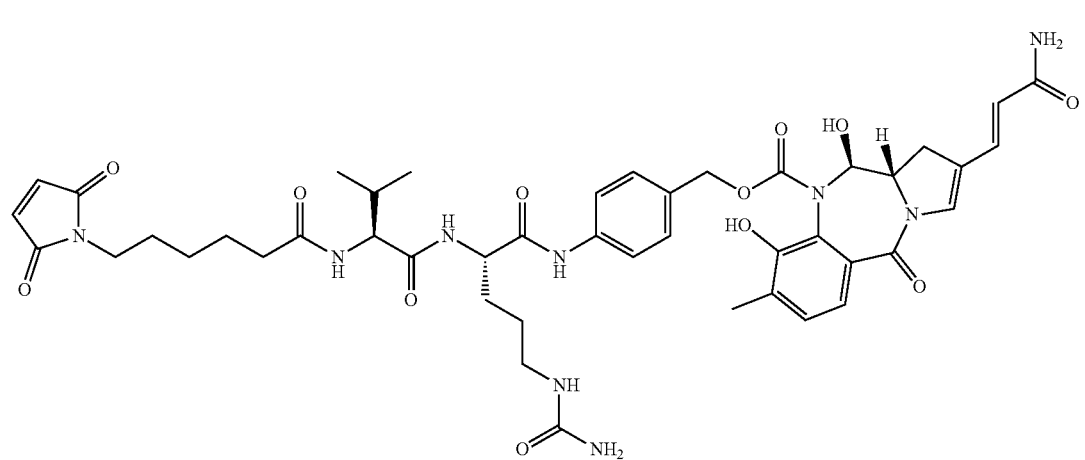
MC-Val-Cit-PAB-anthramycin

(16)
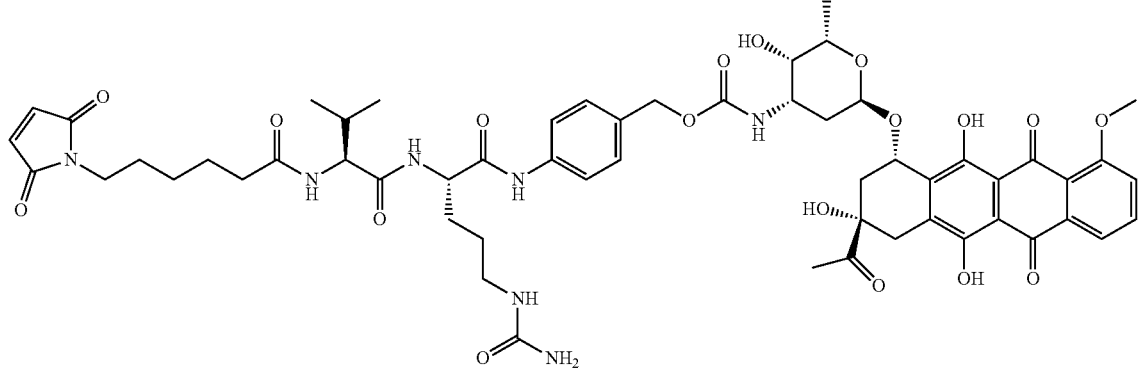
MC-Val-Cit-PAB-daunorubicin
(17)
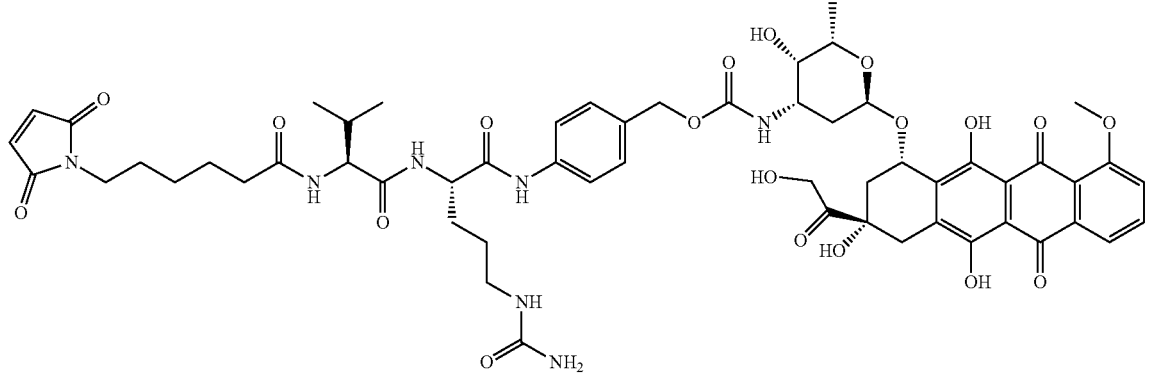
MC-Val-Cit-PAB-doxorubicin
(18)
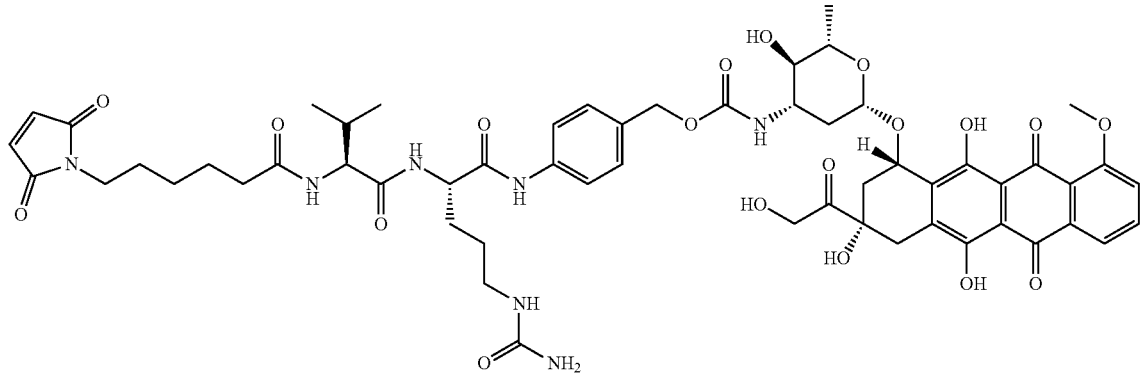
MC-Val-Cit-PAB-epirubicin

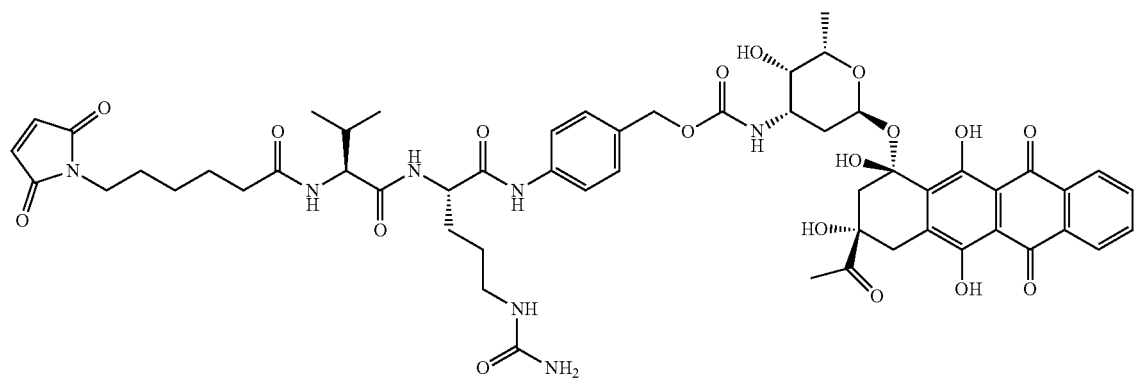
MC-Val-Cit-PAB-idarubicin (19)
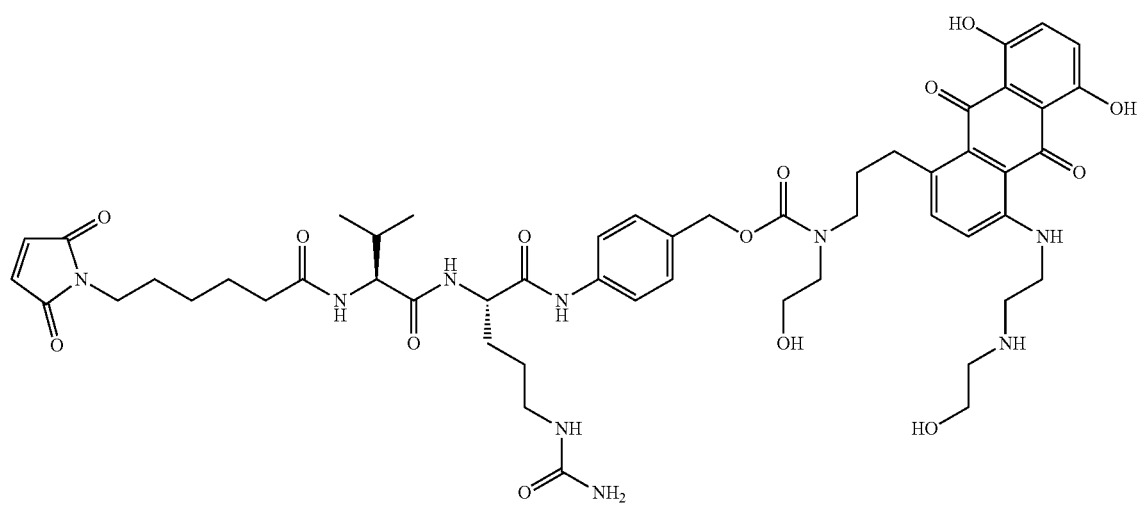
MC-Val-Cit-PAB-mitoxantrone (20)
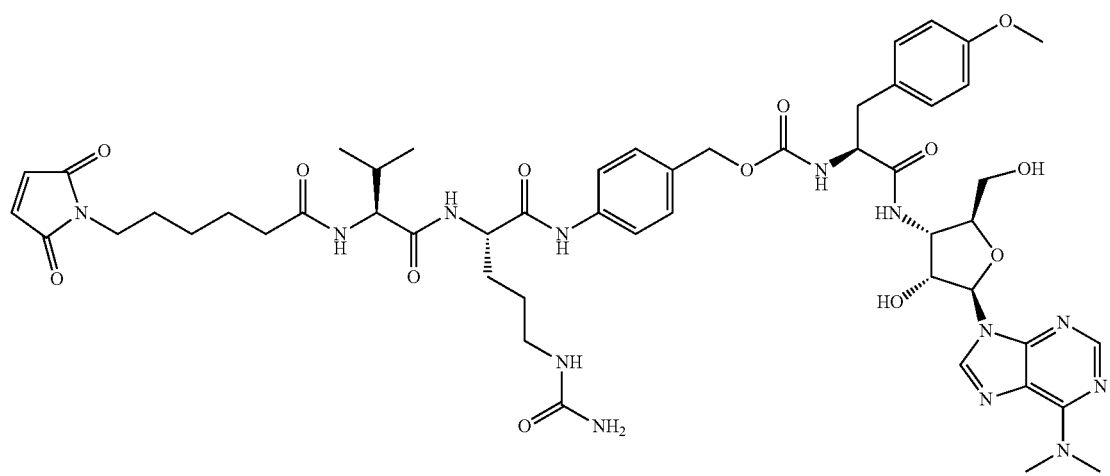
MC-Val-Cit-PAB-puromycin (21)

(22)

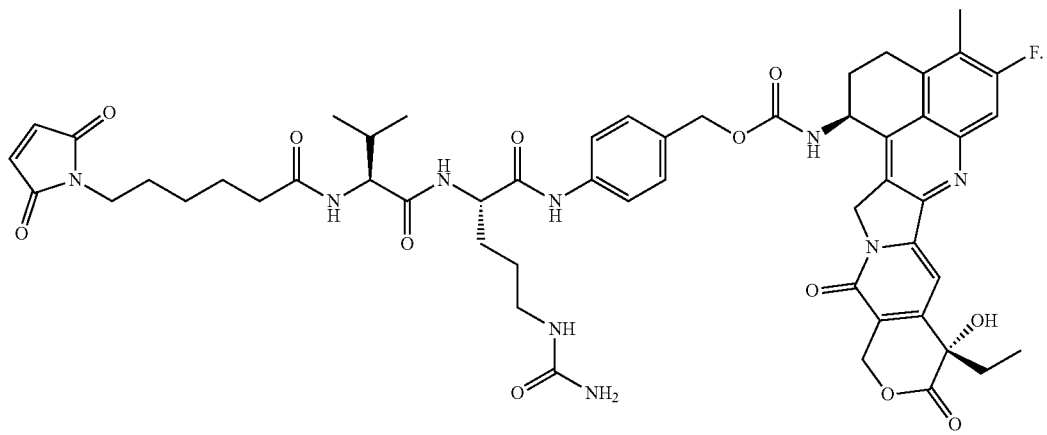

MC-Val-Cit-PAB-DX8951

Further, the organic base 1 and the organic base 2 are each independently one or more of N,N-diisopropylethylamine, triethylamine and pyridine; preferably, the organic base 1 and the organic base 2 are each independently one or two of N,N-diisopropylethylamine and pyridine.

Further, the triazole catalyst is one or more of 1-hydroxybenzotriazole, 1-hydroxy-7-azobenzotriazole, 1-hydroxy-1H-1,2,3-triazole-4-carboxylic acid ethyl ester, and preferably 1-hydroxybenzotriazole.

Further, the reaction temperature of the above reaction is about 15-35° C., and further, the reaction temperature may be 15, 16, 17, 18, 19, 20, 21, 22, 23, 24, 25, 26, 27, 28, 29, 30, 31, 32, 33, 34 or 35° C.

The use of the process described in any one of the above in the preparation of an anti-tumor medicament.

The use of the process described in any one of the above in the preparation of an antibody-drug conjugate.

Compared with the traditional two-step reaction system, the "one-pot process" for preparing intermediate of antibody-drug conjugate provide by the present invention is simple in operation, and needs no such steps as the concentration, washing and filtration of the intermediate reaction liquid, the disposal of the organic waste liquid, and the packaging and storage of the intermediates. After the first step of the reaction is completed, the next reaction operation is carried out directly in the same system and the entire reaction system comprises only one separation and purification process, not only saving costs for consumables, labor, equipment, venues, raw materials, etc., but also greatly reducing the production of waste liquid, reducing the production cost, and improving the production efficiency. In addition, during the reaction process, the linked drug portion is added in the final reaction step, which effectively reduces the consumption of the drug portion (such as MMAD, MMAE or MMAF, DX8951, etc.). Therefore, the "one-pot process" for preparing intermediate of antibody-drug conjugate provided by the present invention is more suitable for scale-up production.

BRIEF DESCRIPTION OF DRAWINGS

FIG. 1 shows a method for preparing a linker-drug conjugate disclosed on page 34 and pages 47-48 of the specification of Chinese Patent Publication No. CN107427591A.

DETAILED DESCRIPTION

Abbreviation

Unless otherwise stated, all abbreviations used in the present invention have the same meaning as understood by those of ordinary skill in the art. As used in the present invention, commonly used abbreviations and their definitions are as follows:

| ABBREVIATION | DEFINE |
| --- | --- |
| MC | Maleimidocaproyl |
| Py | 1,3,5-Triacryloylhexahydro-1,3,5-triazineyl |
| MC-Val-Cit-PAB | Maleimidocaproyl-valine-citrulline-p-amino-benzyloxycarbonyl |
| Py-MAA-Val-Cit-PAB | 1,3,5-Triacryloylhexahydro-1,3,5-triazineyl-mercaptoacetic acid-valine-citrulline-p-amino-benzyloxycarbonyl |
| NPC | bis(4-nitrophenyl)carbonate |
| DIPEA | N,N-diisopropylethylamine |
| HoBt | 1-hydroxybenzotriazole |
| DMF | N,N-dimethylformamide |
| MMAE | |

-continued
| ABBREVIATION | DEFINE |
|---|---|
| MMAD | 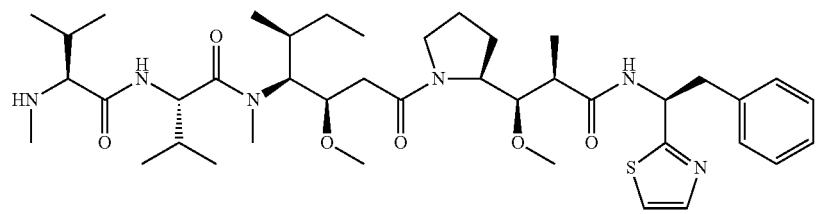 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@@H](NC)C(C)C)C(C)C] |
| MMAF | 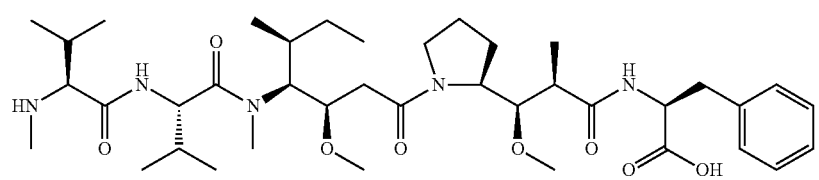 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C] |
| NPC (bis(4-nitrophenyl) carbonate) | 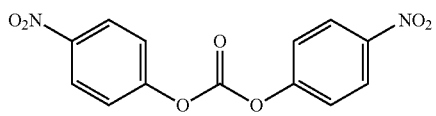<br>bis(4-nitrophenyl) carbonate |
| Anthramycin | 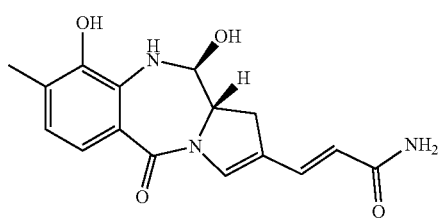 [SMILES: Cc1ccc2c(c1O)N[C@@H](O)[C@@H]1CC(/C=C/C(N)=O)=CN1C2=O] |
| Daunorubicin | 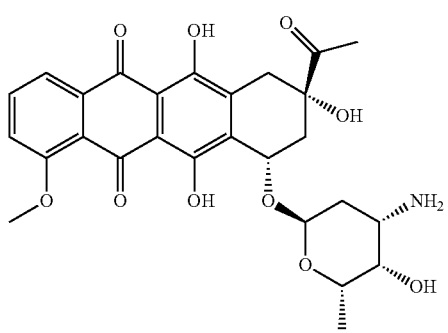 [SMILES: COc1cccc2c1C(=O)c1c(O)c3c(c(O)c1C2=O)C[C@@](O)(C(C)=O)C[C@@H]3O[C@H]1C[C@H](N)[C@H](O)[C@H](C)O1] |
| Doxorubicin | 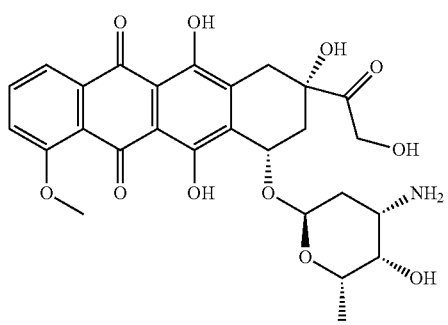 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1] |

| ABBREVIATION | DEFINE |
|---|---|
| Epirubicin | 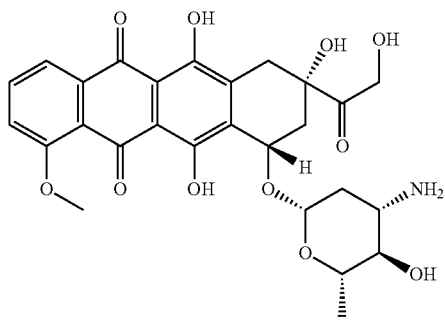 [SMILES: COc1cccc2c1C(=O)c1c(O)c3c(c(O)c1C2=O)C[C@@](O)(C(=O)CO)C[C@@H]3O[C@@H]1C[C@H](N)[C@@H](O)[C@H](C)O1] |
| Idarubicin | 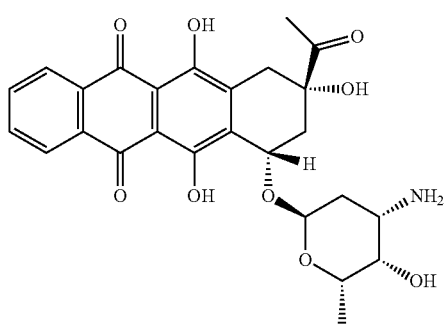 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O] |
| Mitoxantrone | 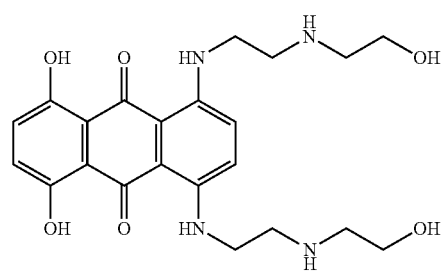 [SMILES: O=C1c2c(O)ccc(O)c2C(=O)c2c(NCCNCCO)ccc(NCCNCCO)c21] |
| Puromycin | 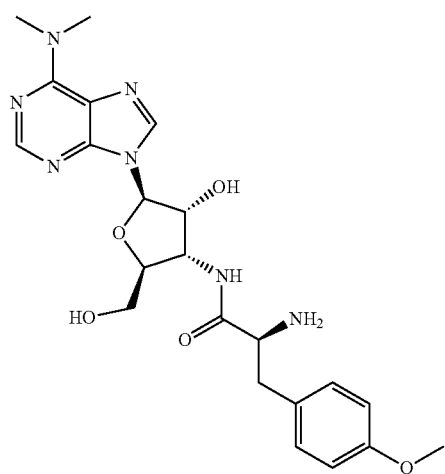 [SMILES: COc1ccc(C[C@H](N)C(=O)N[C@H]2[C@@H](O)[C@H](n3cnc4c(N(C)C)ncnc43)O[C@@H]2CO)cc1] |

| ABBREVIATION | DEFINE |
|---|---|
| DX8951 (Exatecan) | 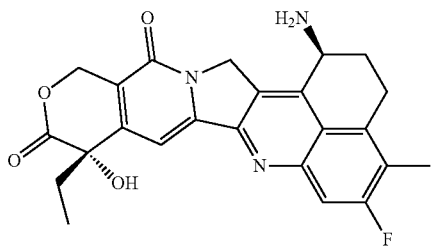 [SMILES: CC[C@@]1(O)C(=O)OCc2c1cc1n(c2=O)Cc2c-1nc1cc(F)c(C)c3c1c2[C@@H](N)CC3] |

Definition

Unless otherwise defined, all technical terms used herein have the same meaning as understood by those of ordinary skill in the art.

The term "antibody-drug conjugate" as used herein refers to a compound in which an antibody/antibody functional fragment, a linker, and a drug portion are linked together through a chemical reaction, and its structure is usually composed of three portions: an antibody or antibody ligand, a drug portion, and a linker that links the antibody or antibody ligand and the drug. At present, the preparation of antibody-drug conjugates usually comprises two steps: in the first step, the linker and the drug portion are chemically reacted to form a "linker-drug" conjugate, and in the second step, the linker portion of the "linker-drug" conjugate is coupled covalently with the antibody/antibody functional fragment via a sulfhydryl group or an amino group. The term "intermediate of antibody-drug conjugate" used herein refers to the above-mentioned "linker-drug" conjugate. Further, the "intermediate of antibody-drug conjugate" mentioned in the present invention generally refers to those "linker-drug" conjugates that are coupled together by a "—CO—NH—" bond formed by amine ester exchange between the linker and the drug.

The terms "linker" and "linker portion" used herein refer to a portion in an antibody-drug conjugate that connects the antibody to the drug, and may be cleavable or uncleavable. A cleavable linker (i.e., a breakable linker or a biodegradable linker) can be broken in or on the target cell, thereby releasing the drug. In some embodiments, the linker of the invention is selected from cleavable linkers, such as disulfide-based linkers (which are selectively cleaved in tumor cells with higher sulfhydryl groups), peptide linkers (which is cleaved by enzymes in tumor cells), and hydrazone linker. In other embodiments, the linkers of the present invention are selected from uncleavable linkers (i.e., unbreakable linkers), such as thioether linkers. In still other embodiments, the linkers of the present invention are a combination of cleavable linkers and unbreakable linker.

The terms "drug" and "drug portion" used herein generally refer to any compound having a desired biological activity and having a reactive functional group in order to prepare the conjugate of the present invention. Desired biological activity includes diagnosis, cure, alleviation, treatment, prevention of diseases in humans or other animals. As new drugs are continuously discovered and developed, these new drugs should also be encompassed by the drugs described in the present invention. Specifically, the drugs include but are not limited to cytotoxic drugs, cell differentiation factors, stem cell nutrition factors, steroid drugs, drugs for treating autoimmune diseases, anti-inflammatory drugs or drugs for infectious diseases. More specifically, the drugs include but are not limited to tubulin inhibitors or DNA and RNA damaging agents.

EXAMPLES

The technical solutions of the present invention will be further described in detail in conjunction with specific embodiments below. It should be pointed out that the following examples are only to illustrate the technical concept and features of the present invention, and the purpose thereof is to enable those skilled in the art to understand the content of the present invention and implement it accordingly, but not to limit the protection scope of the present invention. All equivalent changes or modifications made according to the spirit of the present invention should be covered within the protection scope of the present invention.

General preparation method: Preparation of Py-MAA-Val-Cit-PAB-OH:

(1) Preparation of Py-MAA

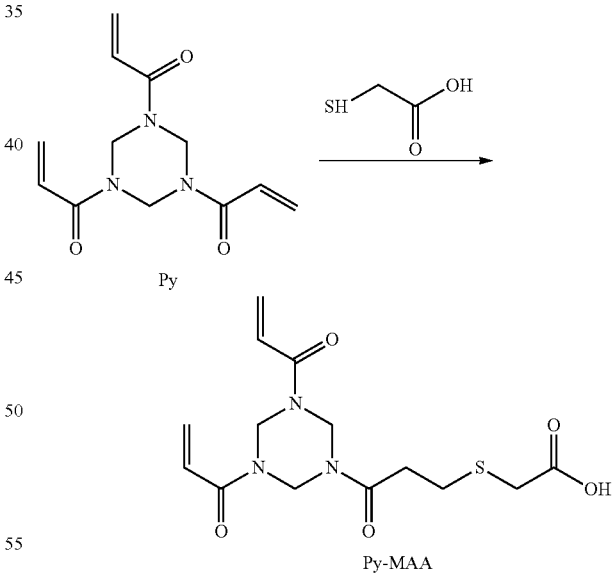

Compound Py (1.87 g, 7.51 mmol) and Et$_3$N (104 µL, 0.75 mmol) were dissolved in anhydrous CH$_2$Cl$_2$ (40 mL), and a solution of thioglycolic acid (103.9 µL, 1.50 mmol) in CH$_2$Cl$_2$ (40 mL) was added dropwise. After the addition, the system was raised to room temperature and stirred overnight. After the reaction was completed, the solvent was removed under vacuum, and the crude product was purified by column chromatography to obtain white solid Py-MAA (1.87 g).

(2) Preparation of Py-MAA-Val-Cit-PAB-OH

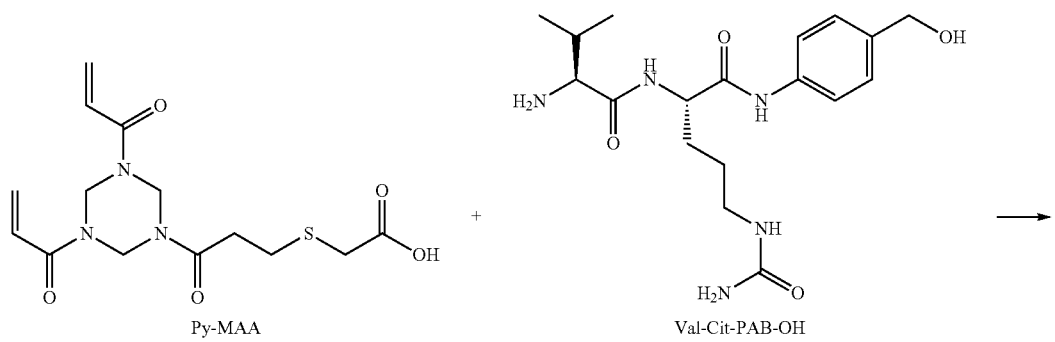

Py-MAA + Val-Cit-PAB-OH →

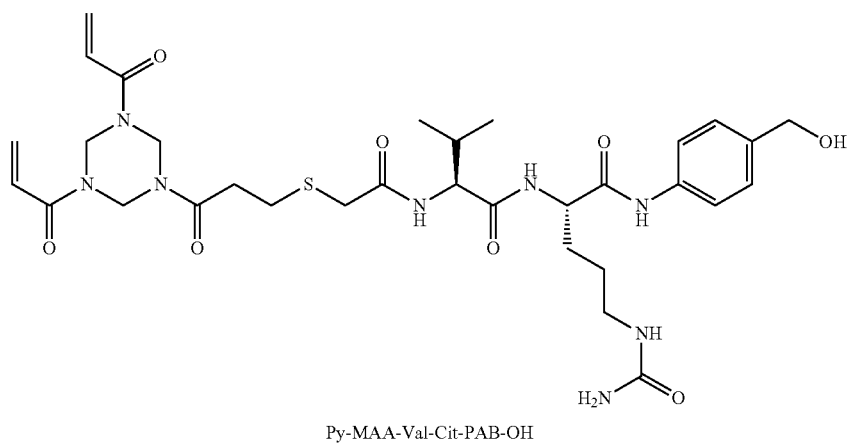

Py-MAA-Val-Cit-PAB-OH

Compound Py-MAA (10.00 g, 29.33 mmol) was placed in tetrahydrofuran (200 mL), and N'N-carbonyldiimidazole (7.13 g, 44.00 mmol) and Val-Cit-PAB-OH (13.34 g, 35.20 mmol) were added, and then the mixture was stirred at room temperature for 24 hours. Petroleum ether (200 mL) was added, and the mixture was stirred for 0.5 hours, and then filtered to obtain a white solid. The white solid was purified by preparative high-performance liquid chromatography, and the preparation liquid was rotary evaporated under reduced pressure to obtain Py-MAA-Val-Cit-PAB-OH (6.67 g, white solid powder).

Example 1

Preparation of Py-MAA-Val-Cit-PAB-MMAE (1) Preparation By "One-Pot Process"

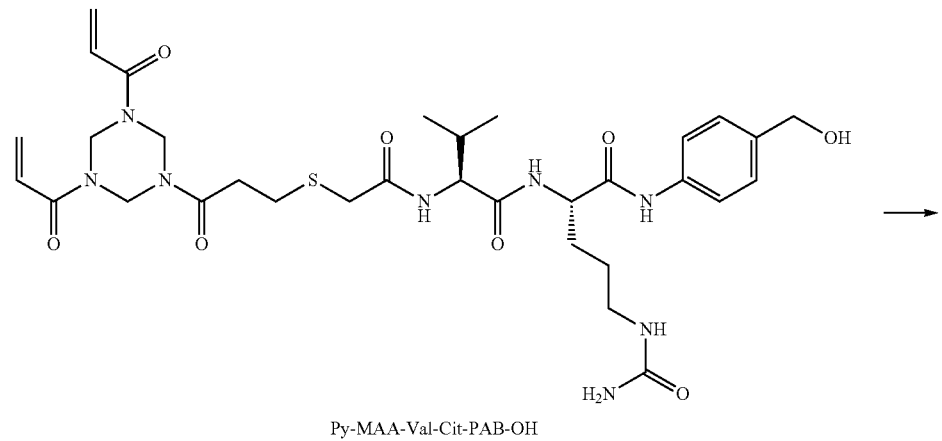

Py-MAA-Val-Cit-PAB-OH

-continued

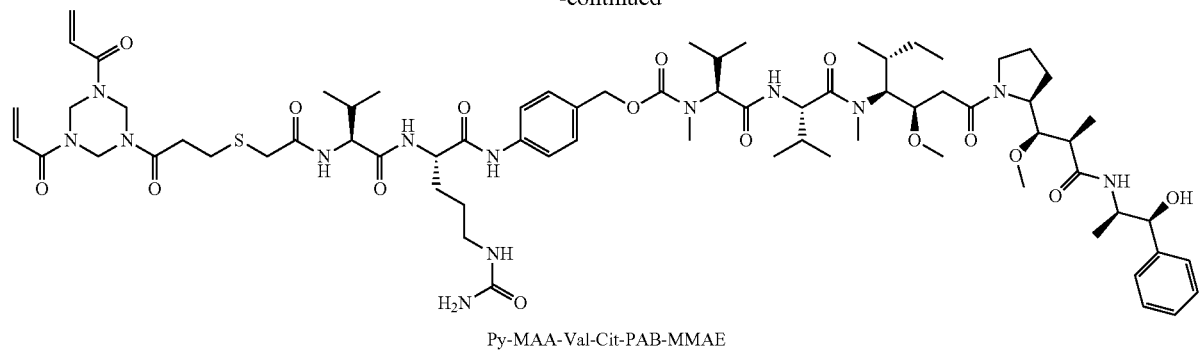
Py-MAA-Val-Cit-PAB-MMAE

Py-MAA-Val-Cit-PAB-OH (1.8 g, 1.0 eq) and DMF (40 mL) were added to a three-necked round-bottom flask in sequence, and after stirring to dissolve, NPC (882 mg, 1.1 eq) and DIPEA (336 mg, 1.0 eq) were added, and the mixture was stirred at 24±2° C. for 24 hours. Then DIPEA (672 mg, 2.0 eq), pyridine (2.3 mL), HoBt (351 mg, 1.0 eq) and MMAE (1.7 g, 0.9 eq) were added to the reaction solution in sequence, and the reaction continued at 24±2° C. for 48 hours. Product Py-MAA-Val-Cit-PAB-MMAE (1.9 g) was obtained after preparative liquid chromatography purification, with a purity of 99.84%, and yield of 51.3% [calculation formula: yield=Py-MAA-Val-Cit-PAB-MMAE amount produced÷(Py-MAA-Val-Cit-PAB-OH amount used÷702.8×1446.8)×100%].

(2) Preparation By "Two-Step Process"

Step 1: Preparation of Py-MAA-Val-Cit-PAB-(4-nitrophenyl)carbonate

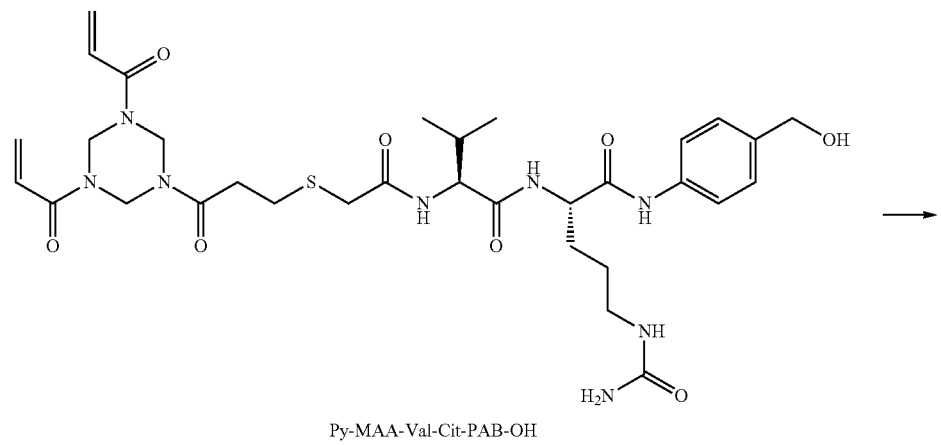
Py-MAA-Val-Cit-PAB-OH

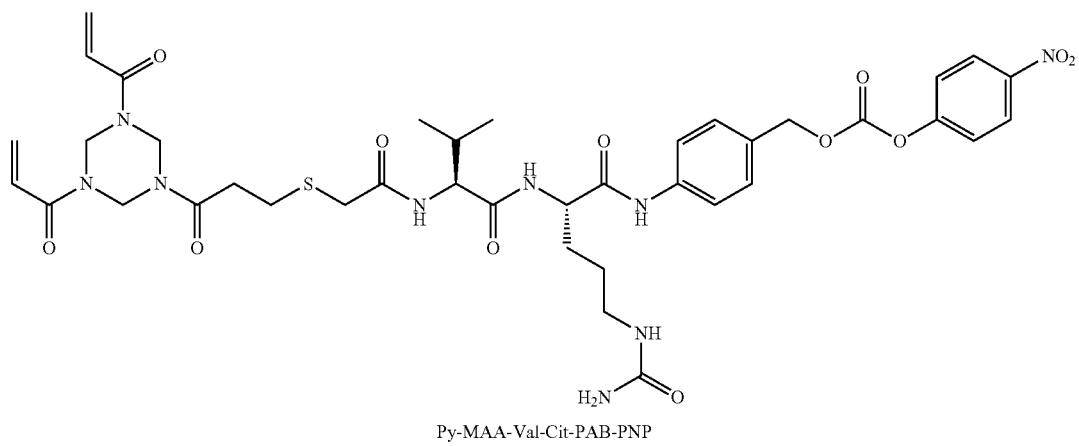
Py-MAA-Val-Cit-PAB-PNP

DMF (40 mL) and Py-MAA-Val-Cit-PAB-OH (1.8 g, 1.0 eq.) were added to a reaction flask, and after stirring to dissolve, bis(4-nitrophenyl)carbonate (NPC, 882 mg, 1.1 eq.) and DIPEA (336 mg, 1.0 eq.) were added and the reaction was performed at 24±2° C. for 24 hours. To the reaction solution, ethyl acetate (mL) was added and petroleum ether (mL) was added dropwise over 20 mins. After the dropwise addition, the mixture was continuously stirred for 10 min and filtered, then washed three times with ethyl acetate and petroleum ether respectively; and spin-dried, to obtain Py-MAA-Val-Cit-PAB-(4-nitrophenyl) carbonate (1.6 g), yield 72.1%, purity: 86%.

Step 2: Preparation of Py-MAA-Val-Cit-PAB-MMAE

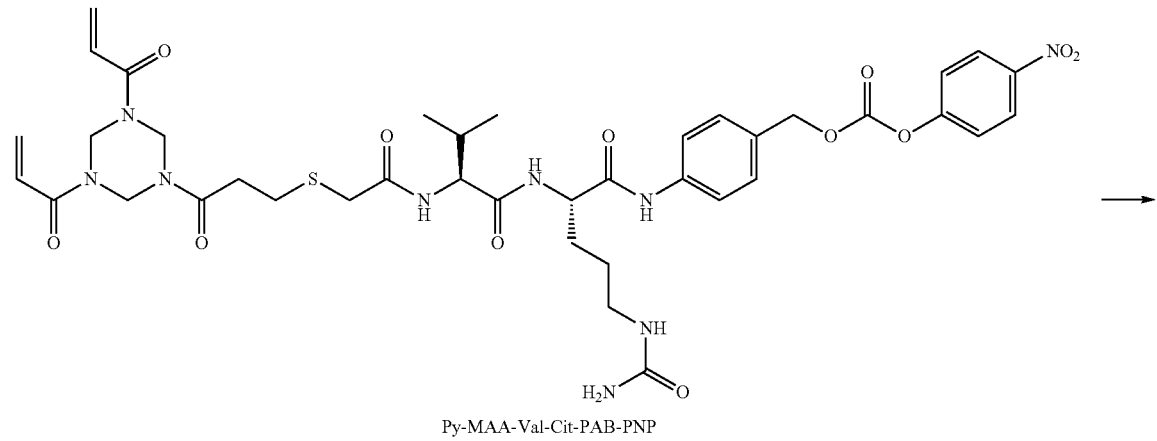

Py-MAA-Val-Cit-PAB-PNP

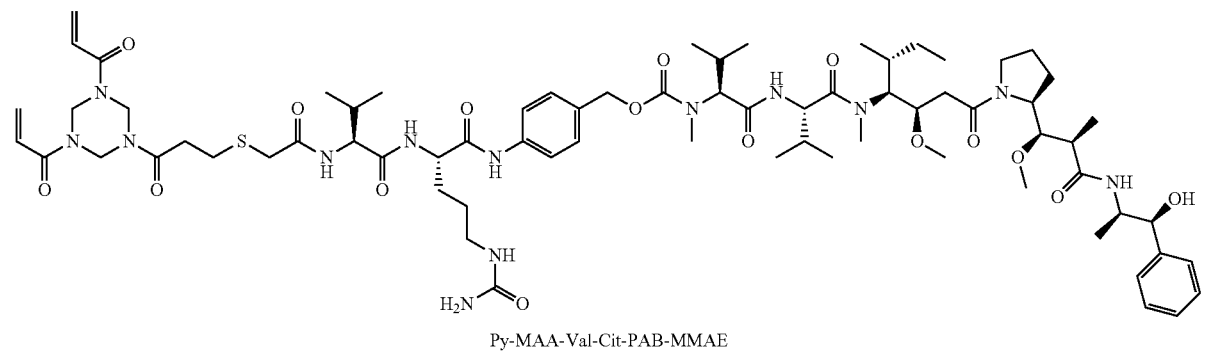

Py-MAA-Val-Cit-PAB-MMAE

Py-MAA-Val-Cit-PAB-(4-nitrophenyl)carbonate (1.5 g), 1-hydroxybenzotriazole (HoBt, 234 mg, 1.0 eq.), DMF (30 mL), MMAE (1.1 g, 0.9 eq.), pyridine (1.5 mL) and DIPEA (447 mg, 2.0 eq) were added to a reaction flask, and the reaction was performed at 24±2° C. for 48 hours and then spin-dried. Then preparative HPLC was performed to obtain Py-MAA-Val-Cit-PAB-MMAE (1.3 g), yield 52%, purity: 99%.

It can be known that the final yield of Py-MAA-Val-Cit-PAB-MMAE prepared by the one-pot process is 51.3%, and the final yield of Py-MAA-Val-Cit-PAB-MMAE prepared by the two-step process is 37.49%, with the same amount of main raw materials. After comparison, the final yield of Py-MAA-Val-Cit-PAB-MMAE prepared by the one-pot process is much greater than that of Py-MAA-Val-Cit-PAB-MMAE prepared by the two-step process.

Example 2

Preparation of Py-MAA-Val-Cit-PAB-MMAD (1) Preparation By "One-Pot Process"

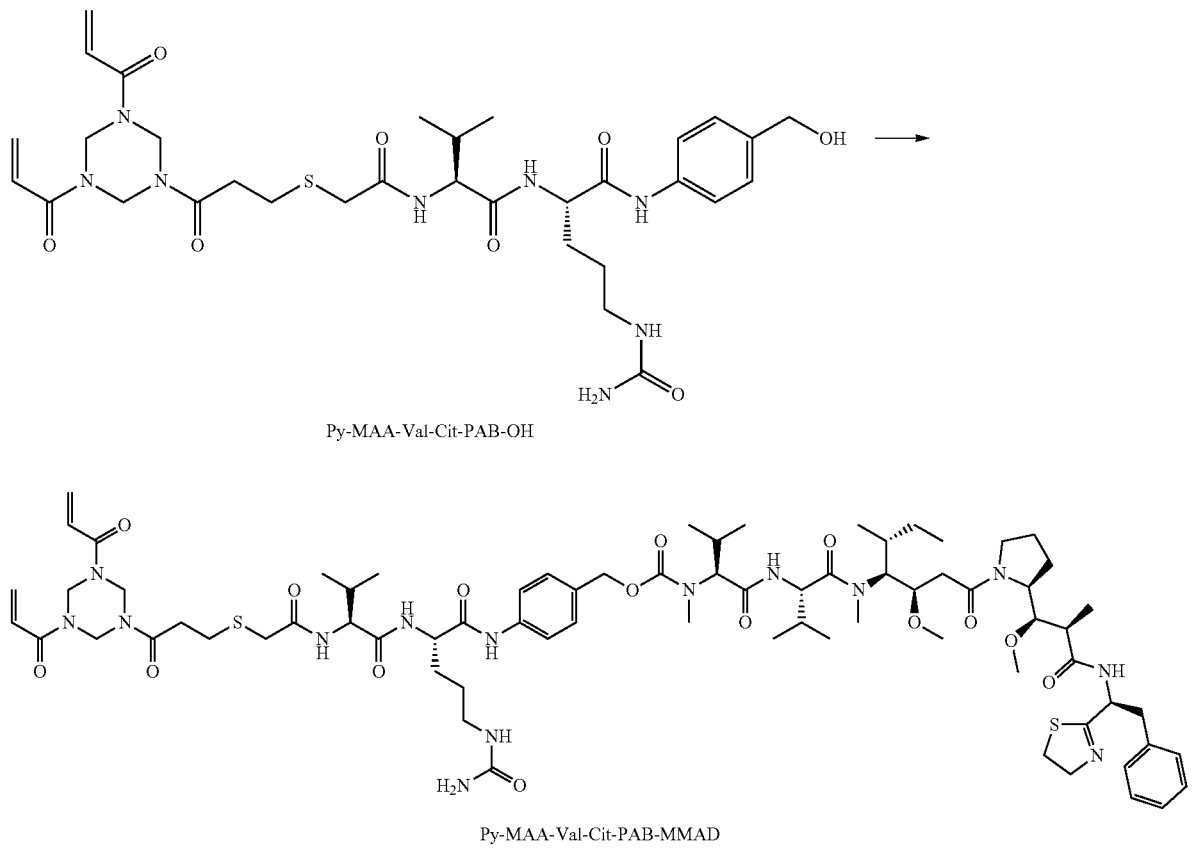 [SMILES: C=CC(=O)N1CN(C(=O)C=C)CN(C(=O)CCSCC(=O)N[C@H](C(=O)N[C@@H](CCCNC(N)=O)C(=O)Nc2ccc(CO)cc2)C(C)C)C1 ; C=CC(=O)N1CN(C(=O)C=C)CN(C(=O)CCSCC(=O)N[C@H](C(=O)N[C@@H](CCCNC(N)=O)C(=O)Nc2ccc(COC(=O)N(C)[C@H](C(=O)N[C@H](C(=O)N(C)[C@@H]([C@H](C)CC)[C@@H](CC(=O)N3CCC[C@H]3[C@H](OC)[C@@H](C)C(=O)N[C@@H](Cc3ccccc3)C3=NCCS3)OC)C(C)C)C(C)C)cc2)C(C)C)C1]

DMF (4 mL) and Py-MAA-Val-Cit-PAB-OH (200 mg, 1.0 eq.) were added to a reaction flask, and after stirring to dissolve, bis(4-nitrophenyl)carbonate (NPC, 95 mg, 1.1 eq.) and DIPEA (36 mg, 1.0 eq.) were added and the reaction was performed at 24±2° C. for 24 hours. 1-hydroxybenzotriazole (HoBt, 38 mg, 1.0 eq.), MMAD (197 mg, 0.9 eq.), pyridine (248 µL) and DIPEA (73 mg, 2.0 eq) were added to the reaction flask, and the reaction was performed at 24±2° C. for 48 hours. The mixture was spin-dried and preparative HPLC was performed to obtain Py-MAA-Val-Cit-PAB-MMAD (208 mg), yield: 48.7%, purity: 99%.

(2) Preparation By "Two-Step Process"

Step 1: Preparation of Py-MAA-Val-Cit-PAB-(4-nitrophenyl)carbonate

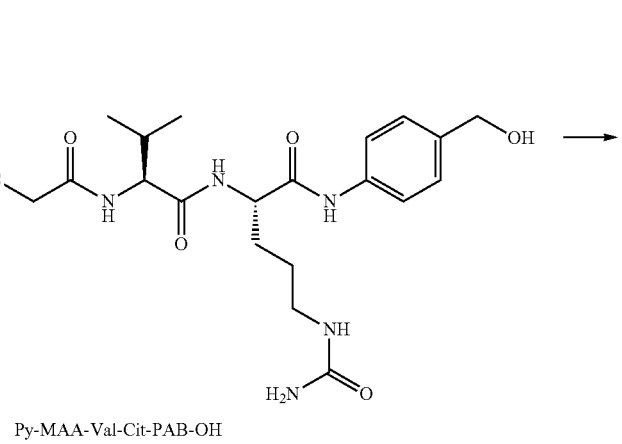

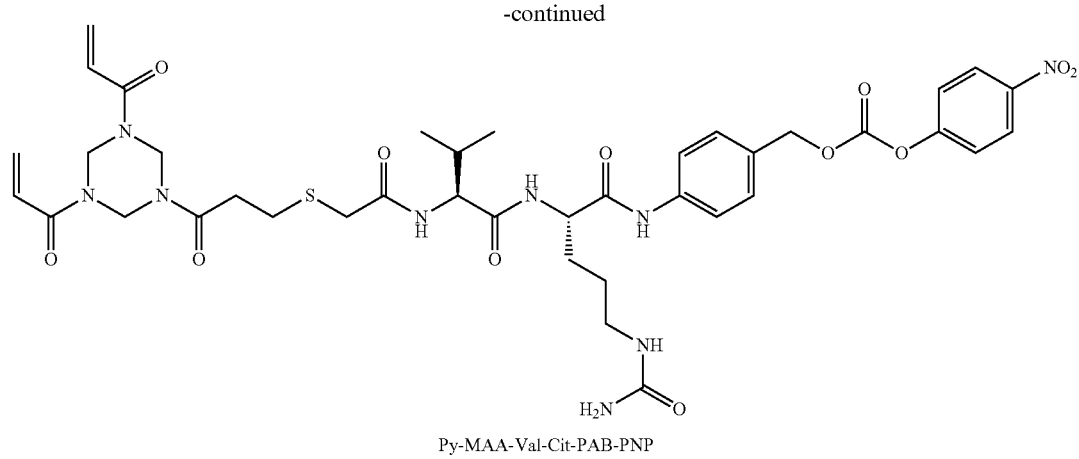

Py-MAA-Val-Cit-PAB-PNP

DMF (4 mL) and Py-MAA-Val-Cit-PAB-OH (200 mg, 1.0 eq.) were added to a reaction flask, and after stirring to dissolve, bis(4-nitrophenyl)carbonate (NPC, 95 mg, 1.1 eq.) and DIPEA (36 mg, 1.0 eq.) were added and the reaction was performed at 24±2° C. for 24 hours. To the reaction solution, ethyl acetate (6 mL) was added and petroleum ether (12 mL) was added dropwise over 20 mins. After the dropwise addition, the mixture was continuously stirred for 10 min and filtered, then washed three times with ethyl acetate and petroleum ether respectively; and spin-dried, to obtain Py-MAA-Val-Cit-PAB-(4-nitrophenyl) carbonate (170 mg), yield: 68.8%, purity: 86%.

Step 2: Preparation of Py-MAA-Val-Cit-PAB-MMAD

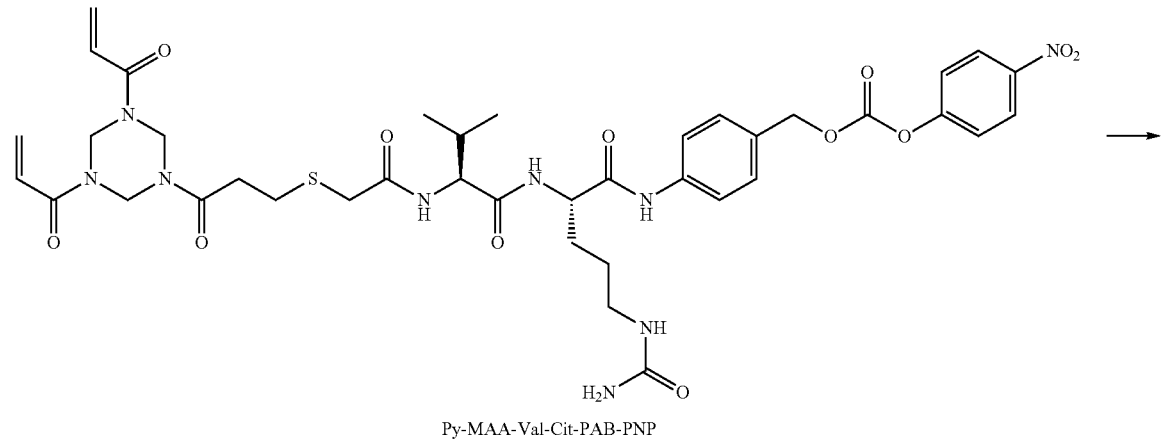

Py-MAA-Val-Cit-PAB-PNP

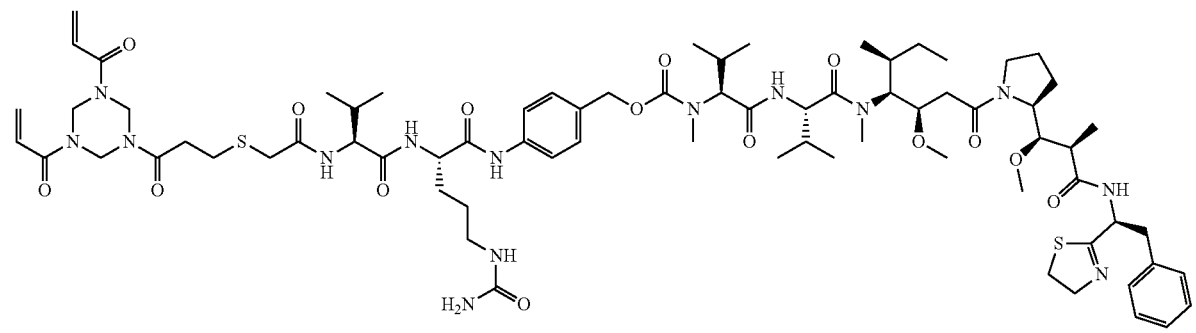

Py-MAA-Val-Cit-PAB-MMAD

Py-MAA-Val-Cit-PAB-(4-nitrophenyl)carbonate (170 mg), 1-hydroxybenzotriazole (HoBt, 27 mg, 1.0 eq.), DMF (4 mL), MMAD (139 mg, 0.9 eq.), pyridine (174 µL) and DIPEA (52 mg, 2.0 eq) were added to a reaction flask, and the reaction was performed at 24±2° C. for 48 hours and then spin-dried. Preparative HPLC was performed to obtain Py-MAA-Val-Cit-PAB-MMAD (139 mg), yield: 47.3%, purity: 99%.

It can be known that the final yield of Py-MAA-Val-Cit-PAB-MMAD prepared by the one-pot process is 48.7%, and the final yield of Py-MAA-Val-Cit-PAB-MMAD prepared by the two-step process is 32.54%, with the same amount of main raw materials. After comparison, the final yield of Py-MAA-Val-Cit-PAB-MMAD prepared by the one-pot process is much greater than that of Py-MAA-Val-Cit-PAB-MMAD prepared by the two-step process.

Example 3

Preparation of Py-MAA-Val-Cit-PAB-DX8951

(1) Preparation By "One-Pot Process"

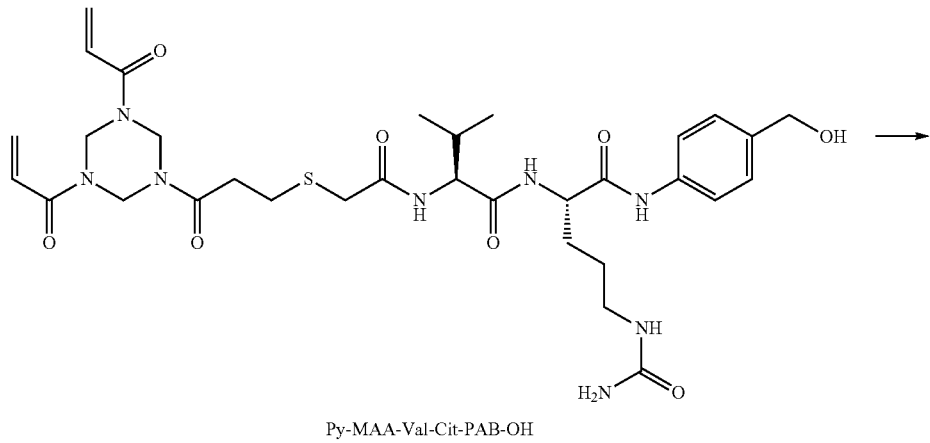

Py-MAA-Val-Cit-PAB-OH

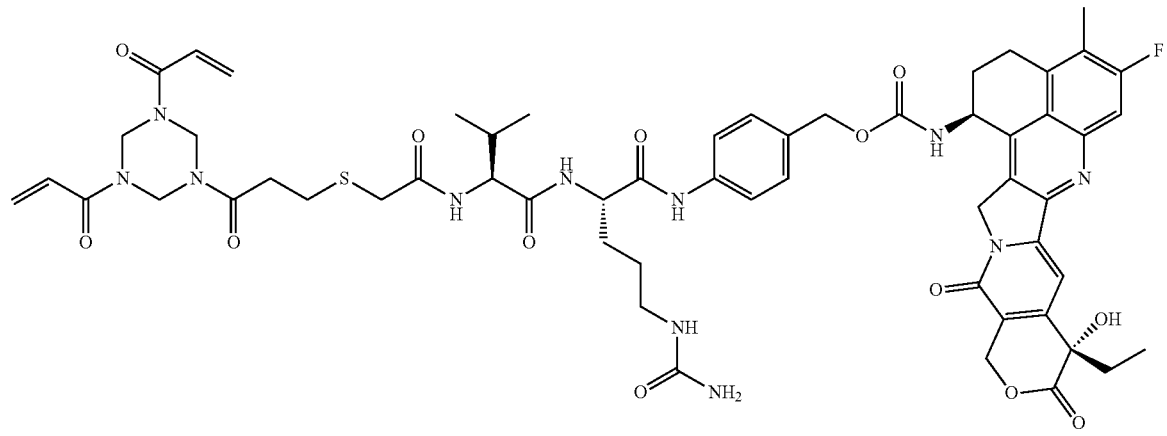

Py-MAA-Val-Cit-PAB-DX8951

DMF (4 mL) and Py-MAA-Val-Cit-PAB-OH (200 mg, 1.0 eq.) were added to a reaction flask, and after stirring to dissolve, bis(4-nitrophenyl)carbonate (NPC, 95 mg, 1.1 eq.) and DIPEA (36 mg, 1.0 eq.) were added and the reaction was performed at 24±2° C. for 24 hours. 1-hydroxybenzotriazole (HoBt, 38 mg, 1.0 eq.), DX8951 (136 mg, 0.9 eq.), pyridine (248 µL) and DIPEA (110 mg, 3.0 eq.) were added, and the reaction continued at 24±2° C. for 48 hours. The mixture was spin-dried and preparative HPLC was performed to obtain Py-MAA-Val-Cit-PAB-DX8951 (123 mg), yield: 37.1%, purity: 97%.

(2) Preparation By "Two-Step Process"
Step 1: Preparation of Py-MAA-Val-Cit-PAB-(4-nitrophenyl)carbonate

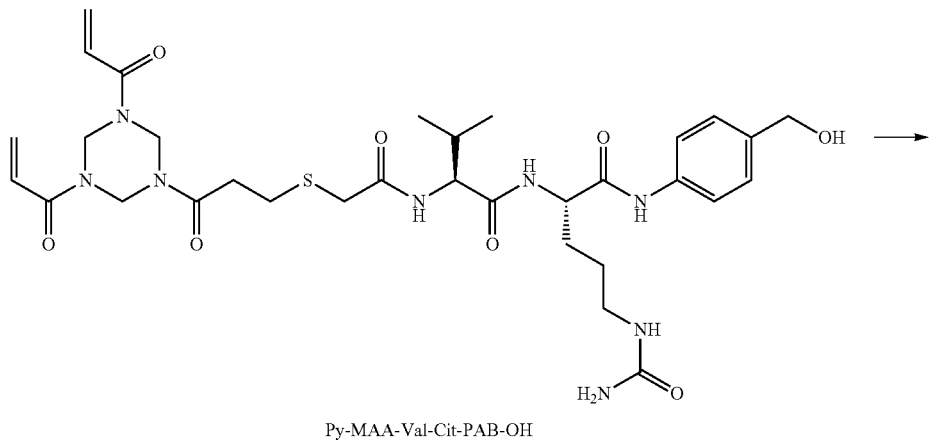

Py-MAA-Val-Cit-PAB-OH

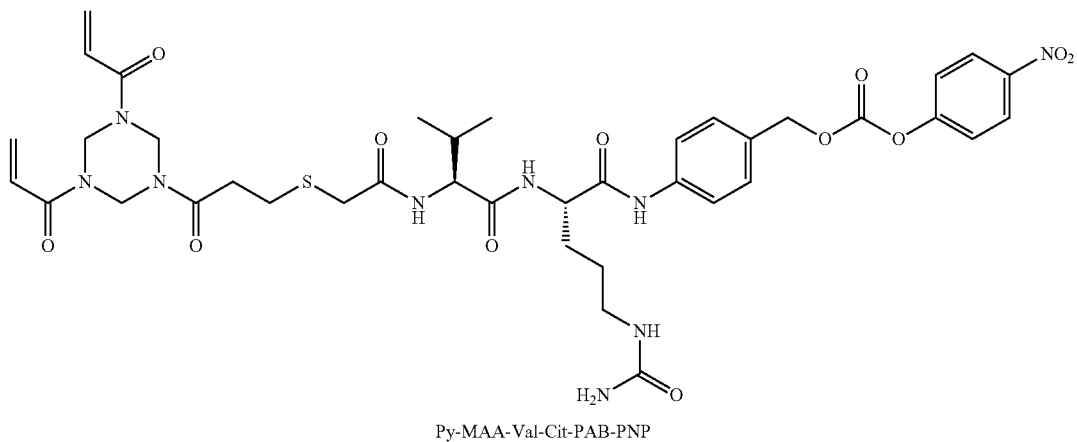

Py-MAA-Val-Cit-PAB-PNP

DMF (4 mL) and Py-MAA-Val-Cit-PAB-OH (200 mg, 1.0 eq.) were added to a reaction flask, and after stirring to dissolve, bis(4-nitrophenyl)carbonate (NPC, 95 mg, 1.1 eq.) and DIPEA (36 mg, 1.0 eq.) were added and the reaction was performed at 24±2° C. for 24 hours. To the reaction solution, ethyl acetate (6 mL) was added and petroleum ether (12 mL) was added dropwise over 20 mins. After the dropwise addition, the mixture was continuously stirred for 10 min and filtered, then washed three times with ethyl acetate and petroleum ether respectively; and spin-dried, to obtain Py-MAA-Val-Cit-PAB-(4-nitrophenyl) carbonate (176 mg), yield: 71.3%, purity: 86%.

Step 2: Preparation of Py-MAA-Val-Cit-PAB-DX8951

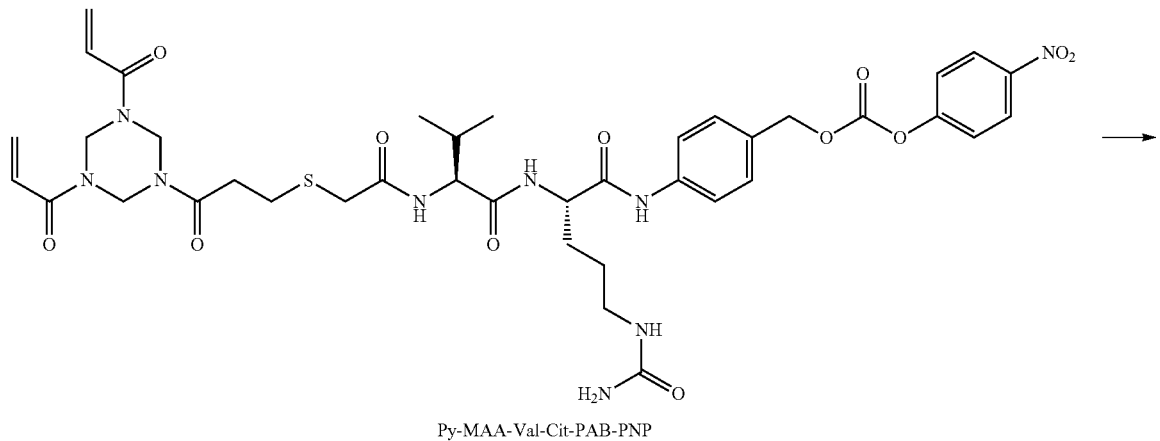

Py-MAA-Val-Cit-PAB-PNP

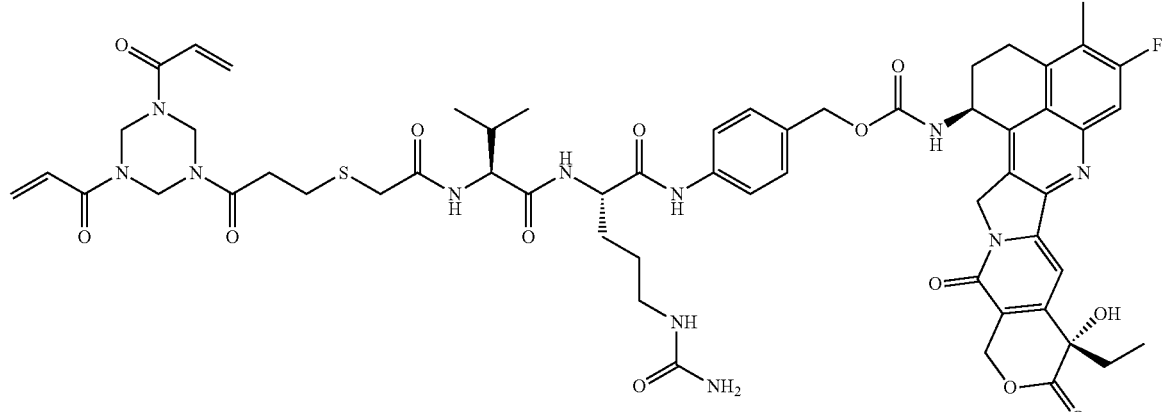

Py-MAA-Val-Cit-PAB-DX8951

Py-MAA-Val-Cit-PAB-(4-nitrophenyl)carbonate (170 mg), 1-hydroxybenzotriazole (HoBt, 27 mg, 1.0 eq.), DMF (4 mL), DX8951 (96 mg, 0.9 eq.), pyridine (174 μL) and DIPEA (78 mg, 3.0 eq) were added to a reaction flask, and the reaction was performed at 24±2° C. for 48 hours and then spin-dried. Preparative HPLC was performed to obtain Py-MAA-Val-Cit-PAB-DX8951 (76 mg), yield: 33.3%, purity: 97%.

It can be known that the final yield of Py-MAA-Val-Cit-PAB-DX8951 prepared by the one-pot process is 37.1%, and the final yield of Py-MAA-Val-Cit-PAB-DX8951 prepared by the two-step process is 23.74%, with the same amount of main raw materials. After comparison, the final yield of Py-MAA-Val-Cit-PAB-DX8951 prepared by the one-pot process is much greater than that of Py-MAA-Val-Cit-PAB-DX8951 prepared by the two-step process.

Example 4

Preparation of Mc-Val-Cit-PAB-MMAD (1) Preparation By "One-Pot Process"

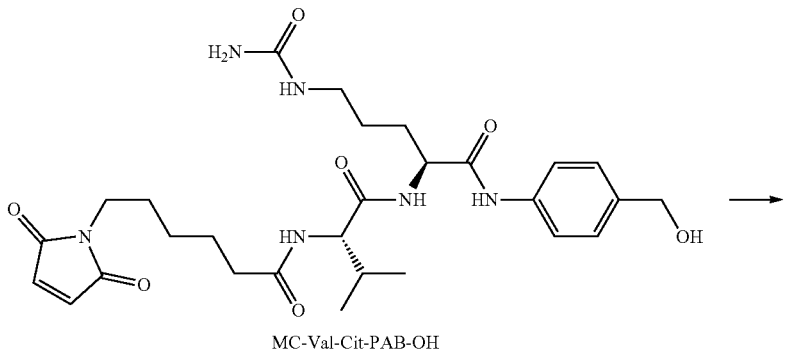

MC-Val-Cit-PAB-OH

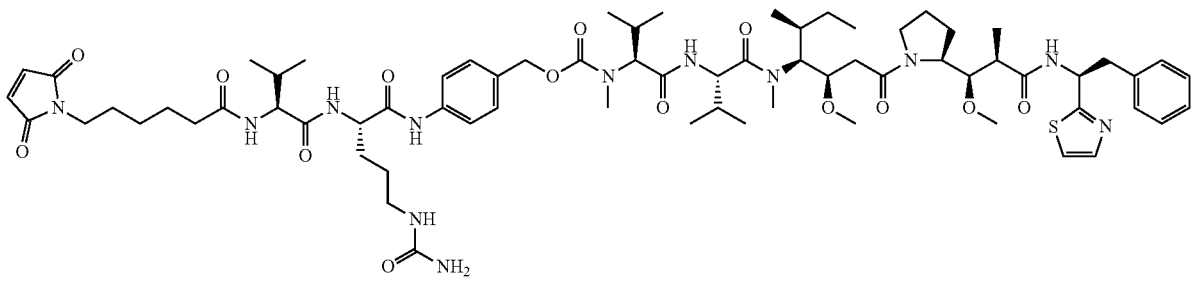

MC-Val-Cit-PAB-MMAD

DMF (4 mL) and MC-Val-Cit-PAB-OH (200 mg, 1.0 eq.) were added to a reaction flask, and after stirring to dissolve, bis(4-nitrophenyl)carbonate (NPC, 116 mg, 1.1 eq.) and DIPEA (45 mg, 1.0 eq.) were added and the reaction was performed at 24±2° C. for 18 hours. 1-hydroxybenzotriazole (HoBt, 47 mg, 1.0 eq.), MMAD (242 mg, 0.9 eq.), pyridine (304 μL) and DIPEA (90 mg, 2.0 eq) were added, and the reaction continued at 24±2° C. for 48 hours. The mixture was spin-dried and preparative HPLC was performed to obtain MC-Val-Cit-PAB-MMAD (228 mg), yield: 47.7%, purity: 99%.

(2) Preparation By "Two-Step Process"

Step 1: Preparation of MC-Val-Cit-PAB-(4-nitrophenyl) carbonate

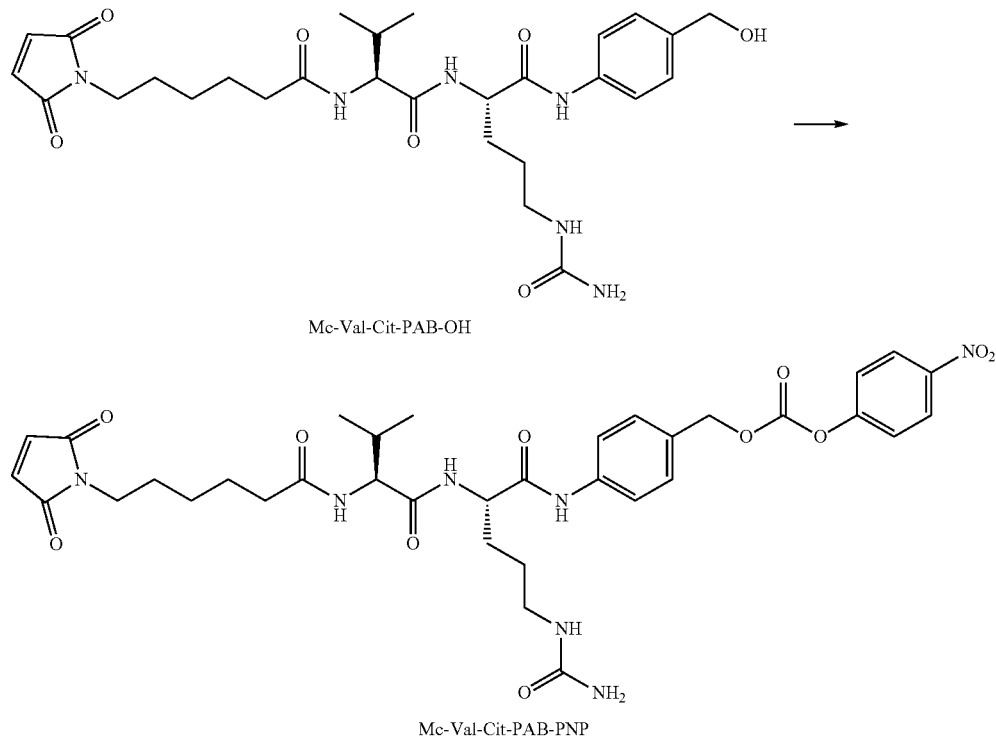

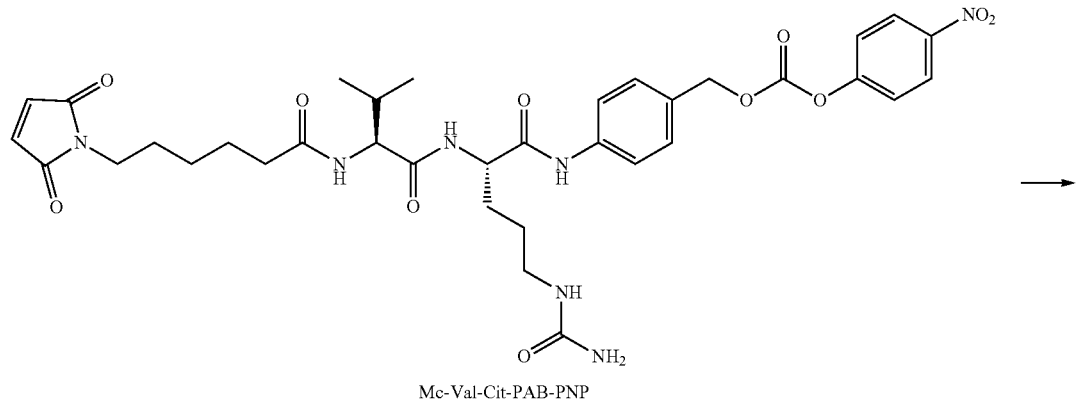

DMF (4 mL) and MC-Val-Cit-PAB-OH (200 mg, 1.0 eq.) were added to a reaction flask, and after stirring to dissolve, bis(4-nitrophenyl)carbonate (NPC, 116 mg, 1.1 eq.) and DIPEA (45 mg, 1.0 eq.) were added. The reaction was performed at 24±2° C. for 18 hours. Ethyl acetate (6 mL) was added and petroleum ether (12 mL) was added dropwise over 20 mins. After the dropwise addition, the mixture was continuously stirred for 10 min and filtered, then washed three times with ethyl acetate and petroleum ether respectively; and spin-dried, to obtain MC-Val-Cit-PAB-(4-nitrophenyl) carbonate (177 mg), yield: 68.6%, purity: 90%.

Step 2: Preparation of MC-Val-Cit-PAB-MMAD

-continued

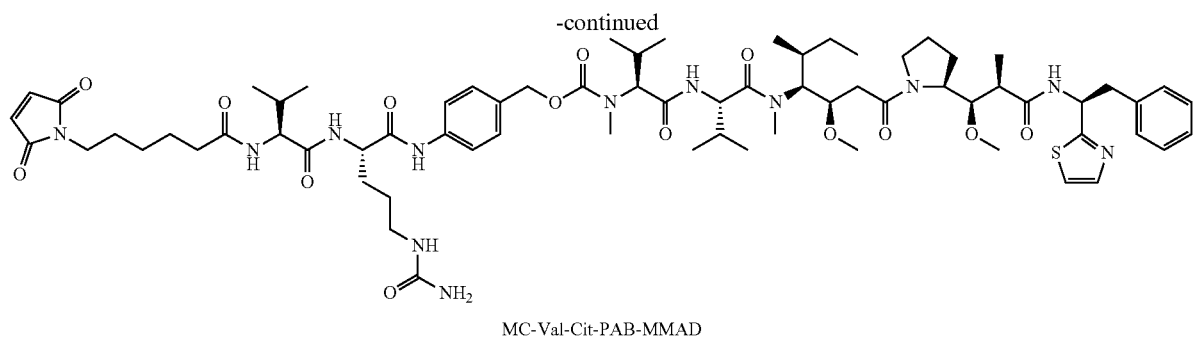

MC-Val-Cit-PAB-MMAD

MC-Val-Cit-PAB-(4-nitrophenyl) carbonate (170 mg) obtained in the first step, 1-hydroxybenzotriazole (HoBt, 31 mg, 1.0 eq), DMF (4 mL), MMAD (160 mg, 0.9 eq.), pyridine (200 μL) and DIPEA (59 mg, 2.0 eq) were added to a reaction flask, and the reaction was performed at 24±2° C. for 48 hours and then spin-dried. Preparative HPLC was performed to obtain MC-Val-Cit-PAB-MMAD (156 mg), yield: 49.4%, purity: 99%.

It can be known that the final yield of MC-Val-Cit-PAB-MMAD prepared by the one-pot process is 47.7%, and the final yield of MC-Val-Cit-PAB-MMAD prepared by the two-step process is 33.88%, with the same amount of main raw materials. After comparison, the final yield of MC-Val-Cit-PAB-MMAD prepared by the one-pot process is much greater than that of MC-Val-Cit-PAB-MMAD prepared by the two-step process.

Example 5

Preparation of Mc-Val-Cit-PAB-DX8951

(1) Preparation By "One-Pot Process"

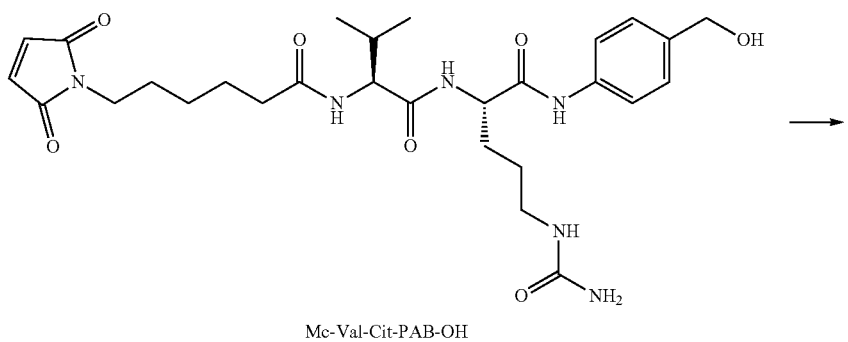

Mc-Val-Cit-PAB-OH

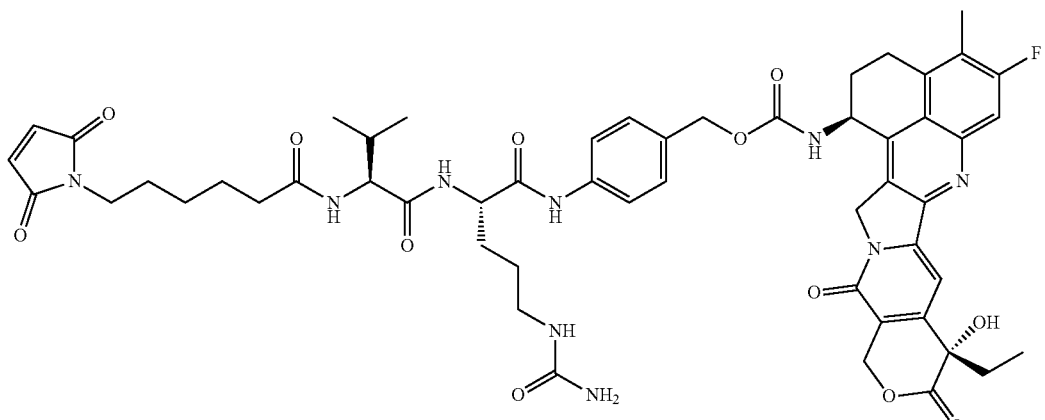

Mc-Val-Cit-PAB-DX8951

DMF (4 mL) and MC-Val-Cit-PAB-OH (200 mg, 1.0 eq.) were added to a reaction flask, and after stirring to dissolve, bis(4-nitrophenyl)carbonate (NPC, 116 mg, 1.1 eq.) and DIPEA (45 mg, 1.0 eq.) were added and the reaction was performed at 24±2° C. for 18 hours. 1-hydroxybenzotriazole (HoBt, 47 mg, 1.0 eq.), DMF (4 mL), DX8951 (167 mg, 0.9 eq.), pyridine (304 μL) and DIPEA (135 mg, 3.0 eq) were added, and the reaction was performed at 24±2° C. for 48 hours. The mixture was spin-dried and preparative HPLC was performed to obtain MC-Val-Cit-PAB-DX8951 (139 mg), yield: 38.4%, purity: 97%.

(2) Preparation By "Two-Step Process"

Step 1: Preparation of MC-Val-Cit-PAB-(4-nitrophenyl) carbonate

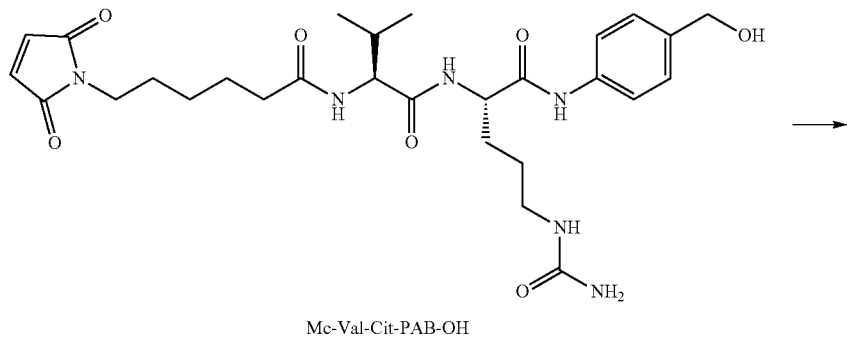

Mc-Val-Cit-PAB-OH

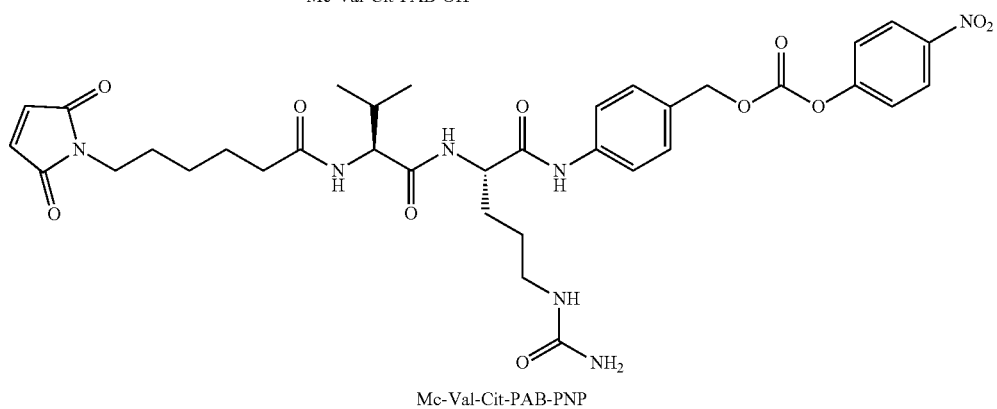

Mc-Val-Cit-PAB-PNP

DMF (4 mL) and MC-Val-Cit-PAB-OH (200 mg, 1.0 eq.) were added to a reaction flask, and after stirring to dissolve, bis(4-nitrophenyl)carbonate (NPC, 116 mg, 1.1 eq.) and DIPEA (45 mg, 1.0 eq.) were added. The reaction was performed at 24±2° C. for 18 hours. Ethyl acetate (6 mL) was added and petroleum ether (12 mL) was added dropwise over 20 mins. After the dropwise addition, the mixture was continuously stirred for 10 min and filtered, then washed three times with ethyl acetate and petroleum ether respectively; and spin-dried, to obtain MC-Val-Cit-PAB-(4-nitrophenyl) carbonate (174 mg), yield: 67.4%, purity: 90%.

Step 2: Preparation of MC-Val-Cit-PAB-DX8951

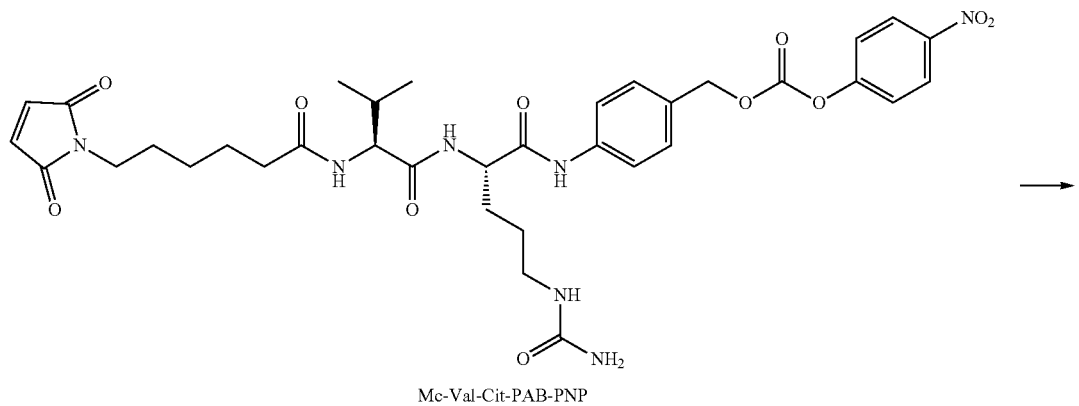

Mc-Val-Cit-PAB-PNP

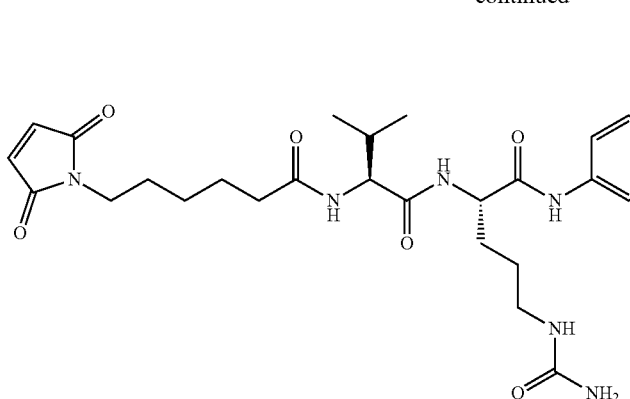

Mc-Val-Cit-PAB-DX8951

MC-Val-Cit-PAB-(4-nitrophenyl) carbonate (170 mg), 1-hydroxybenzotriazole (HoBt, 31 mg, 1.0 eq.), DMF (4 mL), DX8951 (110 mg, 0.9 eq.), pyridine (200 μL) and DIPEA (89 mg, 3.0 eq) were added to a reaction flask, and the reaction was performed at 24±2° C. for 48 hours and then spin-dried. Preparative HPLC was performed to obtain MC-Val-Cit-PAB-DX8951 (85 mg), yield: 35.6%, purity: 97%.

It can be known that the final yield of MC-Val-Cit-PAB-DX8951 prepared by the one-pot process is 38.4%, and the final yield of MC-Val-Cit-PAB-DX8951 prepared by the two-step process is 23.99%, with the same amount of main raw materials. After comparison, the final yield of MC-Val-Cit-PAB-DX8951 prepared by the one-pot process is much greater than that of MC-Val-Cit-PAB-DX8951 prepared by the two-step process.

Example 6

Preparation of Mc-Val-Cit-PAB-MMAE (1) Preparation By "One-Pot Process"

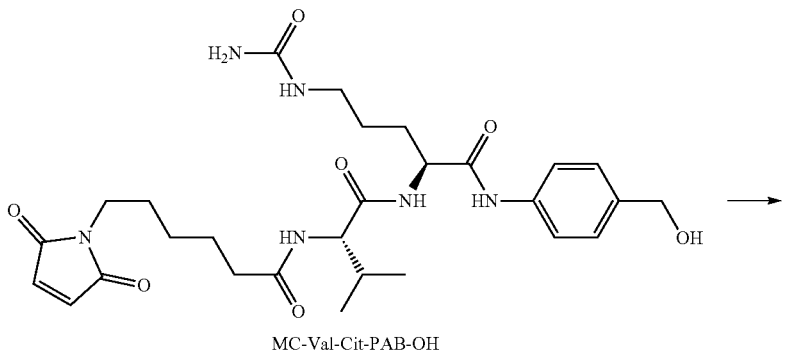

MC-Val-Cit-PAB-OH

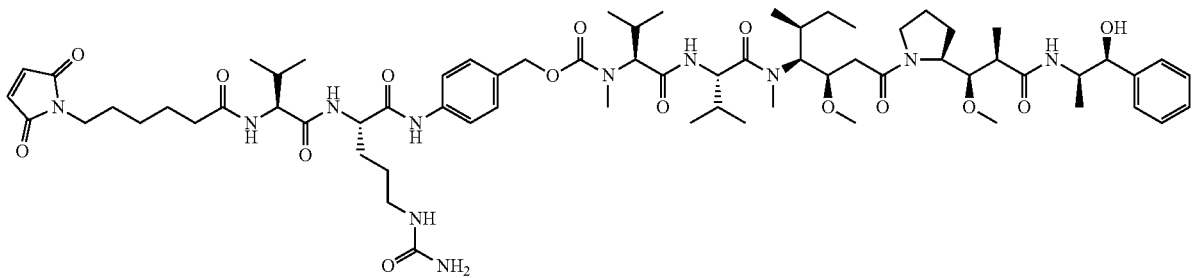

MC-Val-Cit-PAB-MMAE

MC-Val-Cit-PAB-OH (CAS No.: 159857-80-4) (200 mg, 1.0 eq) and DMF (4 mL) were added to a three-necked round-bottom flask in sequence, and after stirring at room temperature to dissolve, NPC (117 mg, 1.1 eq) and DIPEA (45 mg, 1.0 eq) were added, and the mixture was stirred at 24±2° C. for 18 hours. Then DIPEA (90 mg, 2.0 eq), pyridine (0.3 mL, V pyridine/VDIPEA=2.5), HoBt (47 mg, 1.0 eq) and MMAE (251 mg, 1.0 eq) were added to the above reaction solution in sequence, and the reaction continued at 24±2° C. for 48 hours. Product MC-Val-Cit-PAB-MMAE (214 mg) was obtained after preparative liquid chromatography purification, with a purity of 99.45%, and yield of 46.5% [calculation formula: yield=MC-Val-Cit-PAB-MMAE amount produced÷(MC-Val-Cit-PAB-OH amount used÷572.7×1316.6)×100%].

(2) Preparation By "Two-Step Process"

Step 1: Preparation of MC-Val-Cit-PAB-(4-nitrophenyl) carbonate

MC-Val-Cit-PAB-OH (200 mg, 1.0 eq) and DMF (4 mL) were added to a three-necked round-bottom flask in sequence, and after stirring at room temperature to dissolve, NPC (117 mg, 1.1 eq) and DIPEA (45 mg, 1.0 eq) were added and the reaction was performed at 24±2° C. for 18 hours. Ethyl acetate (12 mL) and petroleum ether (18 mL) were added. The mixture was stirred, filtered and spin-dried to obtain a crude product. The crude product was added to acetic acid (2 mL) and methanol (0.3 mL), and after stirring to dissolve, purified water (6 mL) was added dropwise, and the mixture was filtered. The obtained solid was spin-dried on a rotary evaporator to obtain MC-Val-Cit-PAB-(4-nitrophenyl) carbonate (185 mg), yield: 71.8%, purity: 97%.

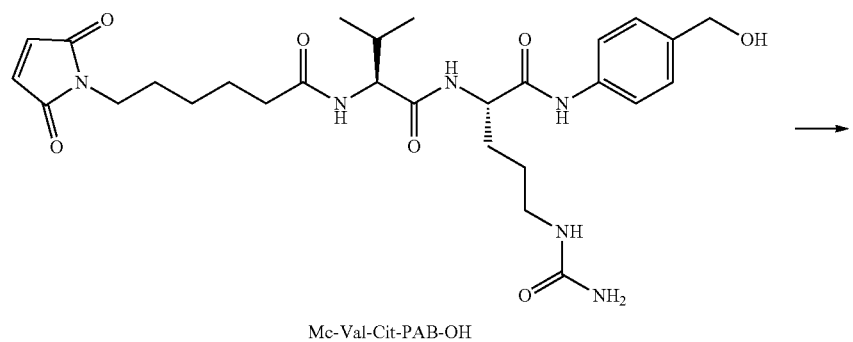

Mc-Val-Cit-PAB-OH

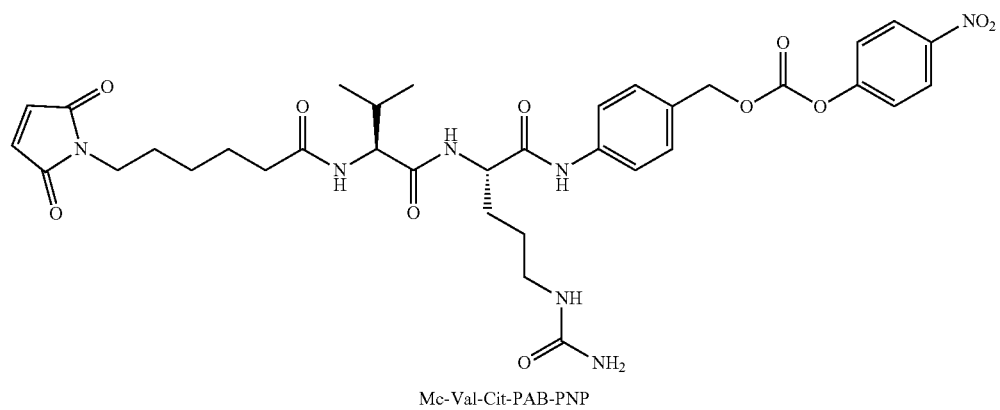

Mc-Val-Cit-PAB-PNP

Step 2: Preparation of MC-Val-Cit-PAB-MMAE

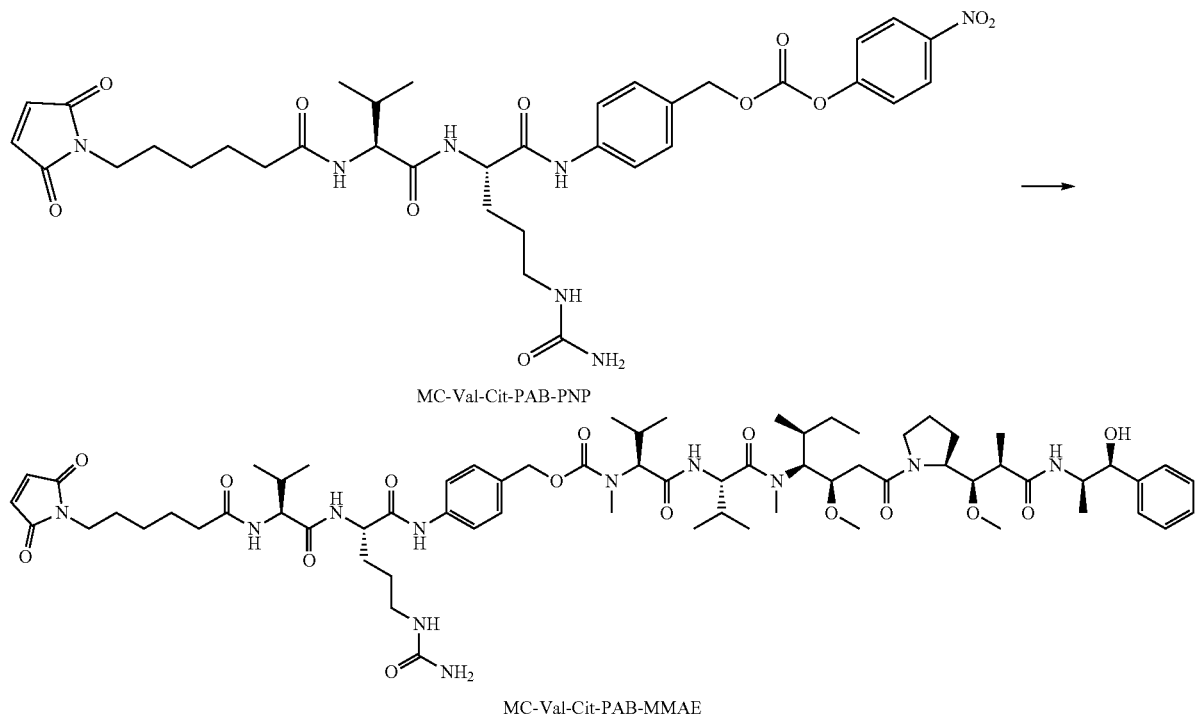

MC-Val-Cit-PAB-PNP

MC-Val-Cit-PAB-MMAE

MC-Val-Cit-PAB-(4-nitrophenyl)carbonate (185 mg), DIPEA (64 mg, 2.0 eq), pyridine (0.2 mL, V pyridine/VDIPEA=2.5), HoBt (34 mg, 1.0 eq) and MMAE (180 mg, 1.0 eq) were added to a reaction flask in sequence, and the reaction was performed at 24±2° C. for 48 hours. Preparative HPLC was performed to obtain the product MC-Val-Cit-PAB-MMAE (115 mg), yield 34.8%, purity 99%.

It can be known that the final yield of MC-Val-Cit-PAB-MMAE prepared by the one-pot process is 46.5%, and the final yield of MC-Val-Cit-PAB-MMAE prepared by the two-step process is 24.99%, with the same amount of main raw materials. After comparison, the final yield of MC-Val-Cit-PAB-MMAE prepared by the one-pot process is much greater than that of MC-Val-Cit-PAB-MMAE prepared by the two-step process.

provided by the present invention is greatly improved relative to that of the existing "two-step process". Since drugs (such as MMAE, DX8951) and similar materials are very expensive, the method of the present invention will greatly reduce the production cost of drugs. Therefore, compared with the prior art "two-step process", the "one pot method" of the present invention has significant progress and unexpected technical effects.

In addition, the one-step preparation process provided by the present invention only needs reactions in the same reaction system, while the traditional preparation process needs reactions in two reaction systems (that is, Py-MAA-Val-Cit-PAB-PNP is extracted and then put into another reaction), which requires the use of organic reagents (ethyl

TABLE 1

Comparison of final yields of "one-pot process" and "two-step process"

| product | Total yields of "one-pot process" | Total yields of "two-step process" | Absolute increase of the yield | Relative increase of the yield |
| --- | --- | --- | --- | --- |
| Py-MAA-Val-Cit-PAB-MMAE | 51.30% | 37.49% | 13.81% | 36.84% |
| Py-MAA-Val-Cit-PAB-MMAD | 48.70% | 32.54% | 16.16% | 49.66% |
| Py-MAA-Val-Cit-PAB-DX8951 | 37.10% | 23.74% | 13.36% | 56.28% |
| Mc-Val-Cit-PAB-MMAD | 47.70% | 33.88% | 13.82% | 40.79% |
| Mc-Val-Cit-PAB-DX8951 | 38.40% | 23.99% | 14.41% | 60.07% |
| Mc-Val-Cit-PAB-MMAE | 46.50% | 24.99% | 21.51% | 86.07% |

Note:
Absolute increase of the yield = Total yields of "one-pot process" - Total yields of "two-step process"
Relative increase of the yield = (Total yields of "one-pot process" - Total yields of "two-step process) / Total yields of "two-step process";

By comparison of the total yields of the "one-pot process" and the total yields of the "two-step process" for Py-MAA-Val-Cit-PAB-MMAE, Py-MAA-Val-Cit-PAB-MMAD, Py-MAA-Val-Cit-PAB-DX8951, Mc-Val-Cit-PAB-MMAD, Mc-Val-Cit-PAB-DX8951, and Mc-Val-Cit-PAB-MMAE, it can be found that the final yield of "one-pot process"

acetate and petroleum ether, etc.) and equipment (for concentration) and a new reaction vessel (for the next reaction), undoubtedly bringing a lot of work to the synthesis process. The use of additional organic reagents and recycling operations not only requires more manpower, but also has a certain impact on the environment. Therefore, the one-step preparation process provided by the present invention is more suitable for large-scale production.
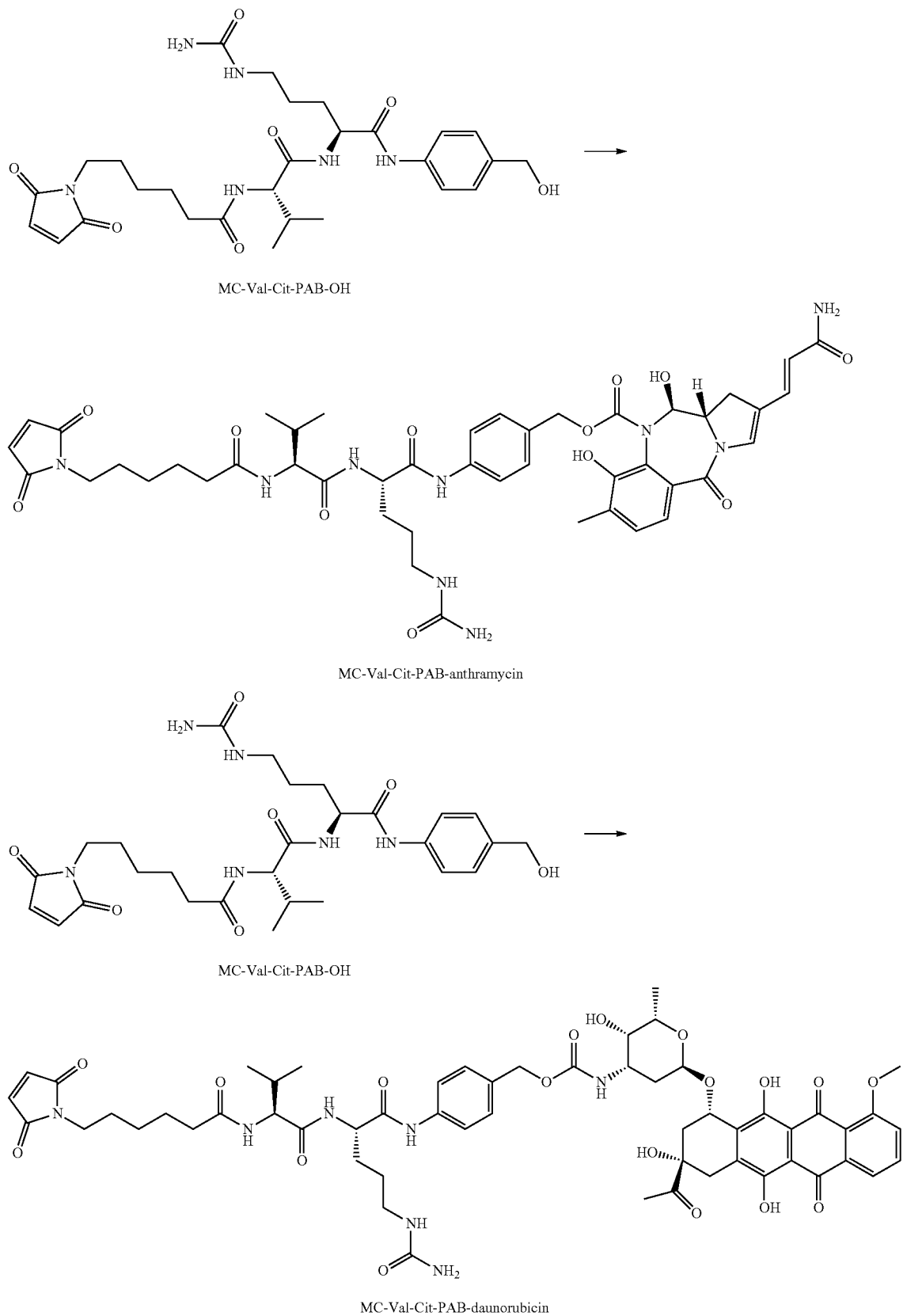
MC-Val-Cit-PAB-OH
MC-Val-Cit-PAB-anthramycin
MC-Val-Cit-PAB-OH
MC-Val-Cit-PAB-daunorubicin

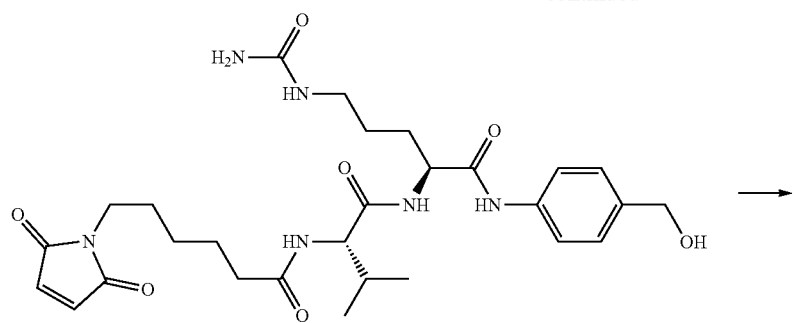
MC-Val-Cit-PAB-OH
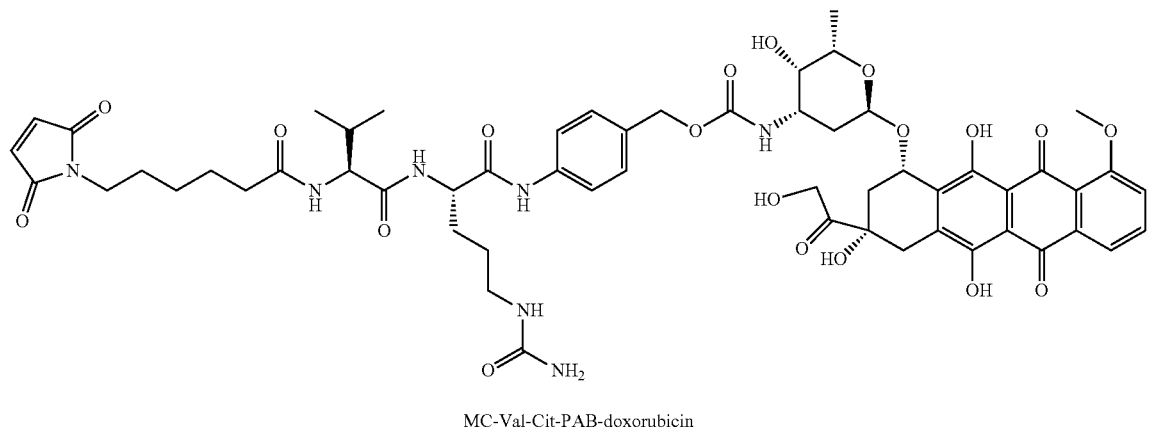
MC-Val-Cit-PAB-doxorubicin
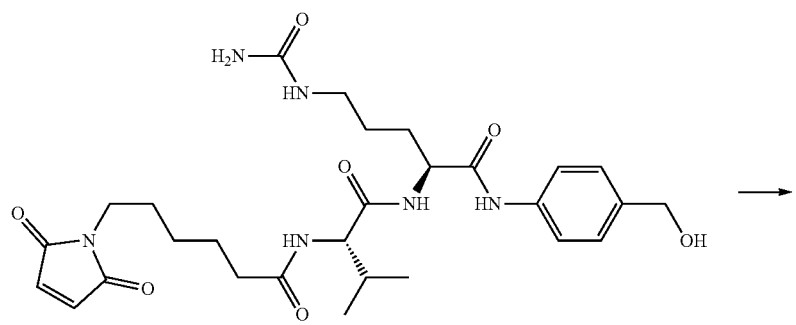
MC-Val-Cit-PAB-OH
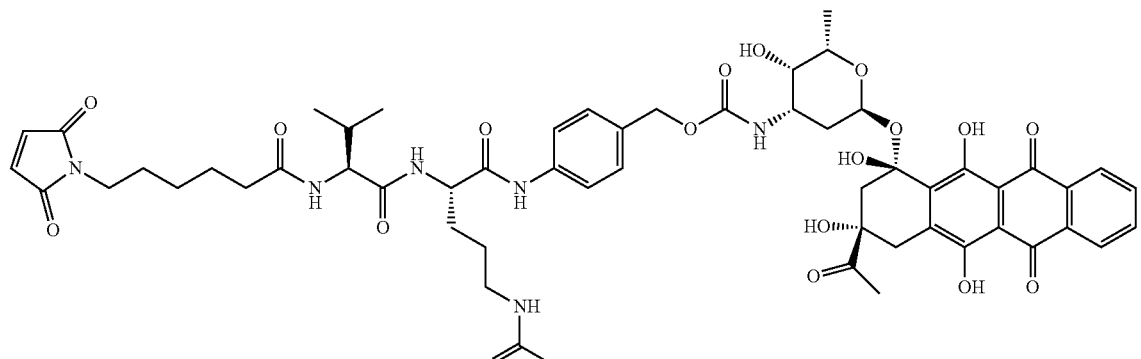
MC-Val-Cit-PAB-idarubicin

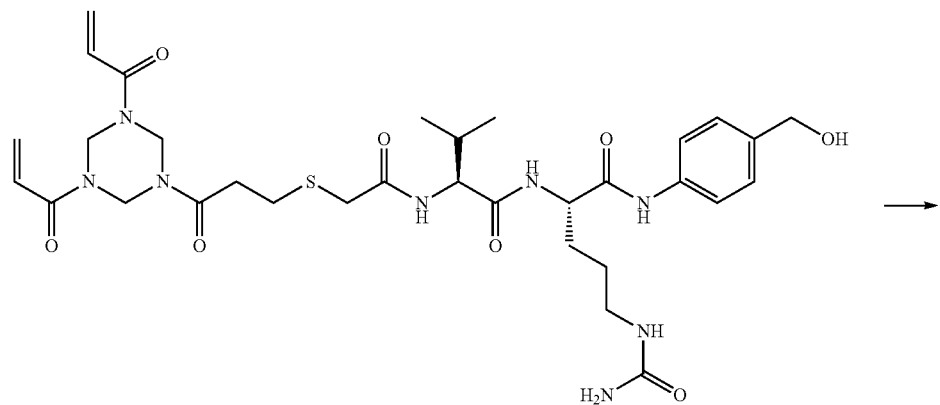
Py-MAA-Val-Cit-PAB-OH
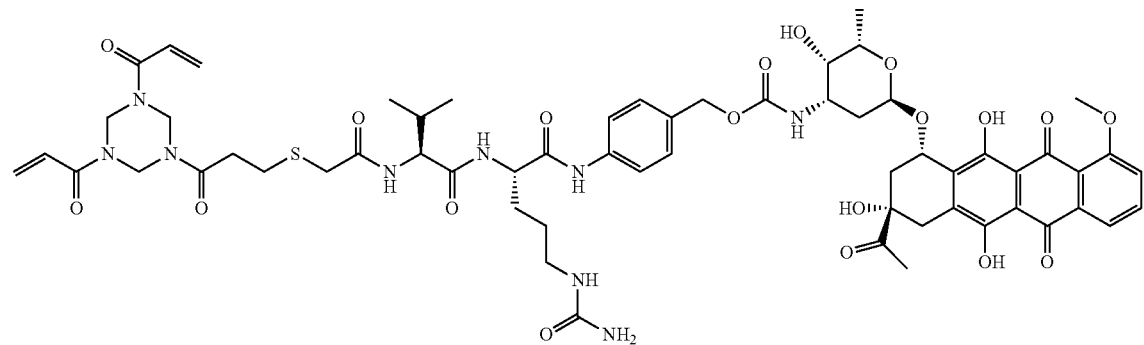
Py-MAA-Val-Cit-PAB-daunorubicin
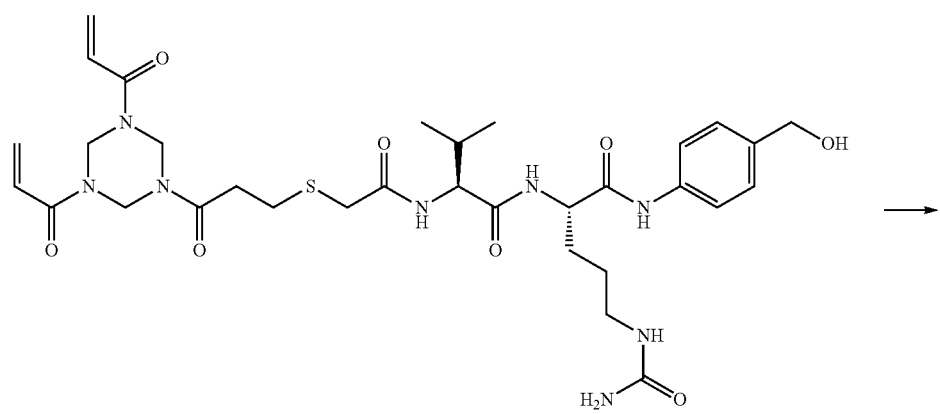
Py-MAA-Val-Cit-PAB-OH
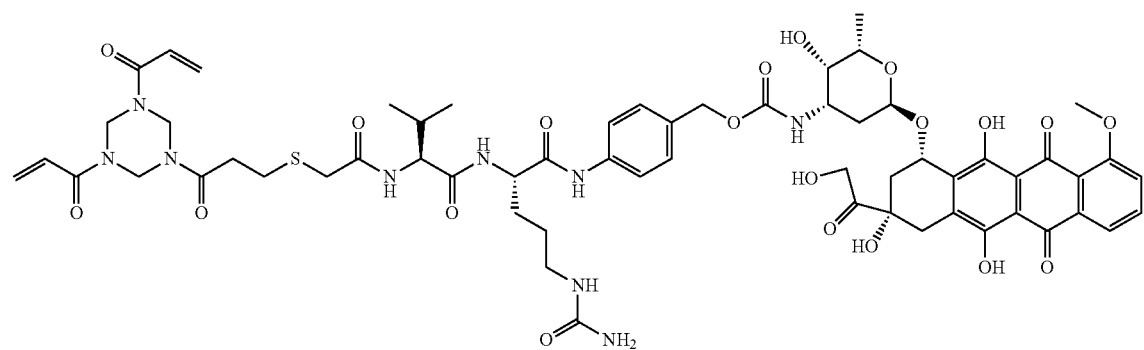
Py-MAA-Val-Cit-PAB-doxorubicin -continued

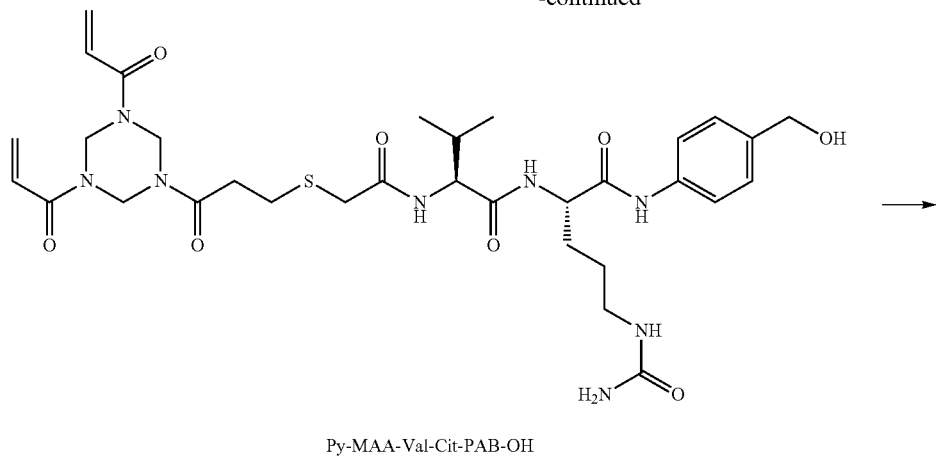

Py-MAA-Val-Cit-PAB-OH

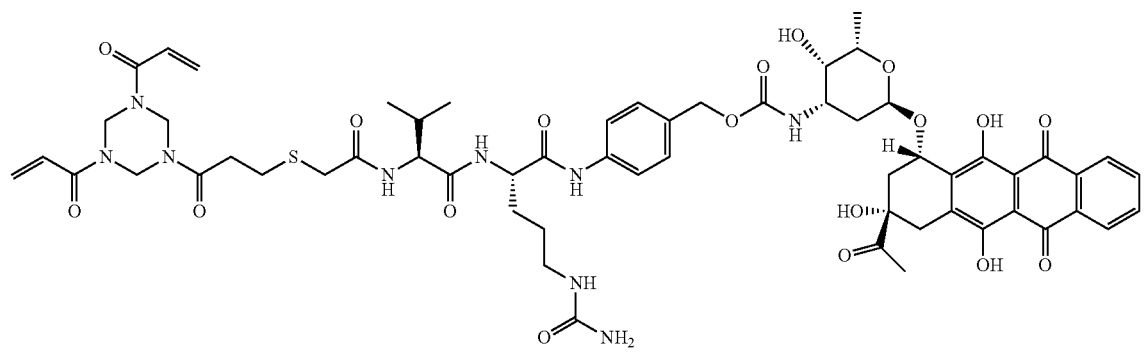

Py-MAA-Val-Cit-PAB-idarubicin

The present invention has been exemplified by various specific examples. However, those skilled in the art can understand that the present invention is not limited to various specific embodiments. Those skilled in the art can make various modifications or changes to the present invention, and various technical features mentioned throughout the text can be combined with each other without departing from the spirit and scope of the present invention. Such changes and modifications are within the scope of the present invention.

The invention claimed is:

1. A process for preparing an intermediate of antibody-drug conjugate comprising a linker portion and a drug portion, wherein the intermediate of antibody-drug conjugate is Py-MAA-Val-Cit-PAB-D or MC-Val-Cit-PAB-D, wherein Py-MAA-Val-Cit-PAB or MC-Val-Cit-PAB in the intermediate is the linker portion, and D in the intermediate represents linked drug portion comprising free amino groups, wherein the process comprises the following reaction route:

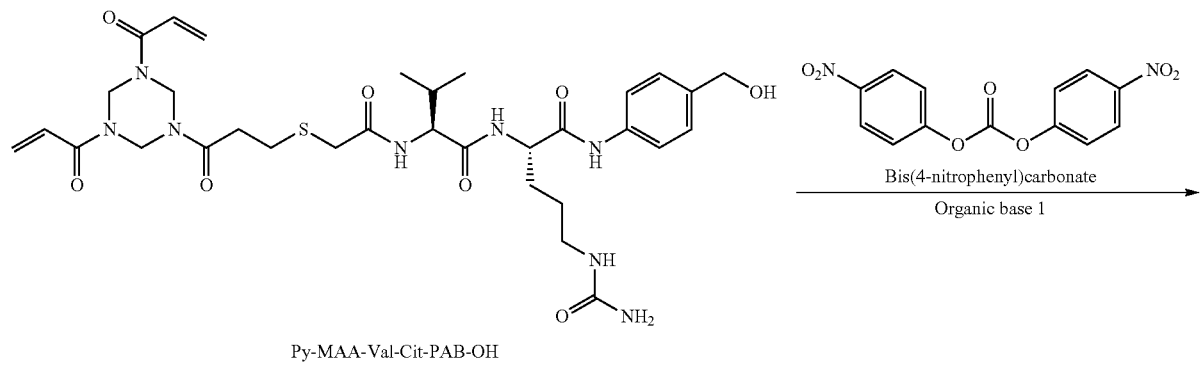

Py-MAA-Val-Cit-PAB-OH

-continued
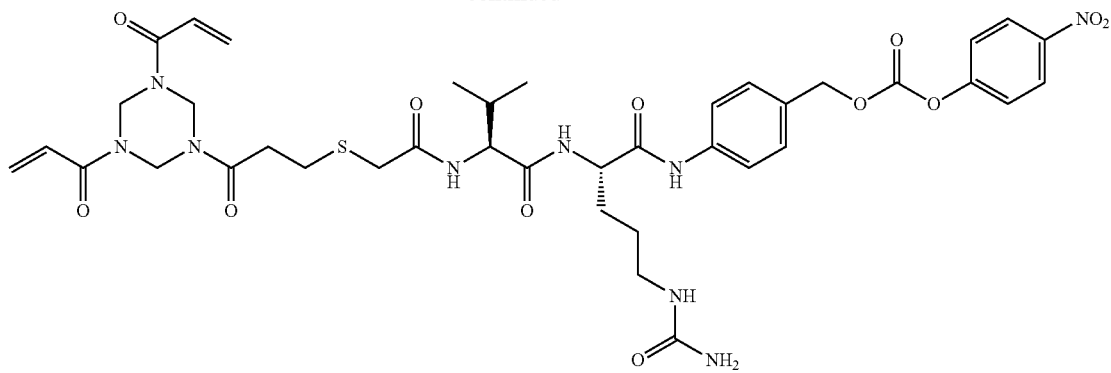
Py-MAA-Val-Cit-PAB-PNP
Drug portion D | i) Triazole catalyst
ii) Organic base 2
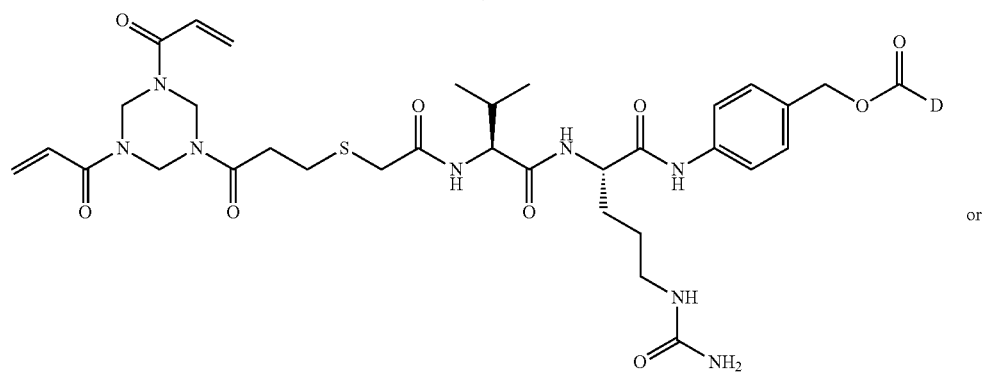
Py-MAA-Val-Cit-PAB-D
or
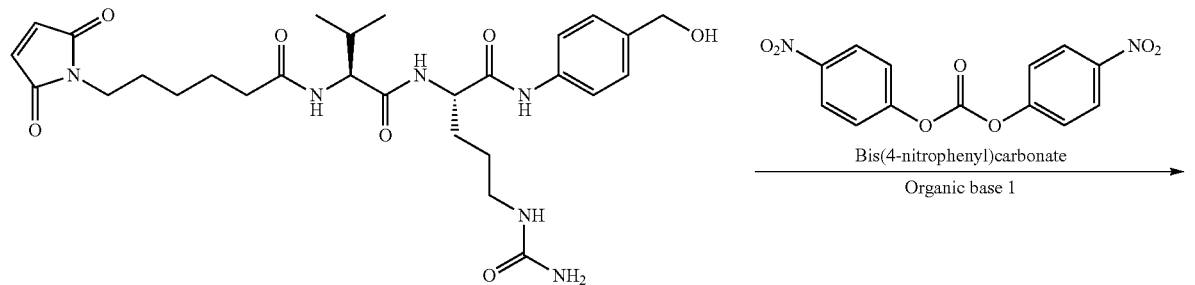
Mc-Val-Cit-PAB-OH
Bis(4-nitrophenyl)carbonate
Organic base 1
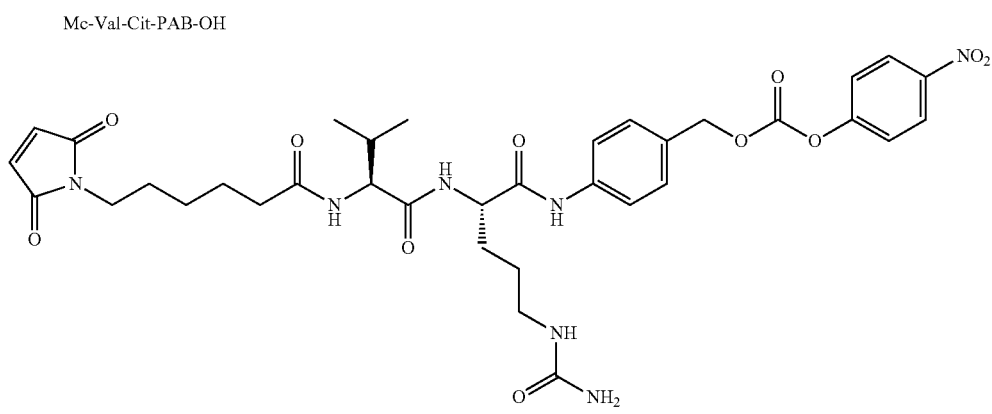
Mc-Val-Cit-PAB-PNP
Drug portion D | i) Triazole catalyst
ii) Organic base 2

-continued

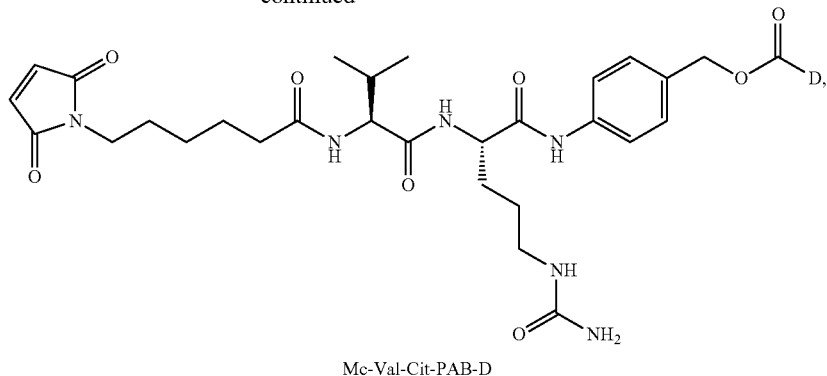

Mc-Val-Cit-PAB-D wherein the preparation process is a one-pot process in which two steps are carried out in one system, wherein, the organic base 1 and the organic base 2 are each independently one or two of N,N-diisopropylethylamine and pyridine, and wherein the triazole catalyst is one or more of 1-hydroxybenzotriazole, 1-hydroxy-7-azobenzotriazole, 1-hydroxy-1H-1,2,3-triazole-4-carboxylic acid ethyl ester.

2. The process according to claim 1, comprising reacting Py-MAA-Val-Cit-PAB-OH or MC-Val-Cit-PAB-OH with bis(4-nitrophenyl)carbonate (NPC) in the presence of an organic base, and after the completion of the above reaction, further adding organic base, and then adding 1-hydroxybenzotriazole and the drug portion D into the reaction system for further reaction.

3. The process according to claim 1, wherein the drug portion D is auristatin cytotoxic agent, anthramycin cytotoxic agent, anthracycline cytotoxic agents or puromycin cytotoxic agent, or camptothecin analogs.

4. The process according to claim 3, wherein the auristatin cytotoxic agent is MMAE, MMAF, MMAD or derivatives thereof; the anthramycin cytotoxic agent is anthramycin or derivative thereof; the anthracycline cytotoxic agent is daunorubicin, doxorubicin, epirubicin, idarubicin, mitoxantrone or derivatives thereof; the puromycin cytotoxic agent is puromycin or derivative thereof; and the camptothecin analogue is DX8951 or derivative thereof.

5. The process according to claim 4, wherein Py-MAA-Val-Cit-PAB-D or MC-Val-Cit-PAB-D has a structure as shown in the following formulas (1-22):

(1)

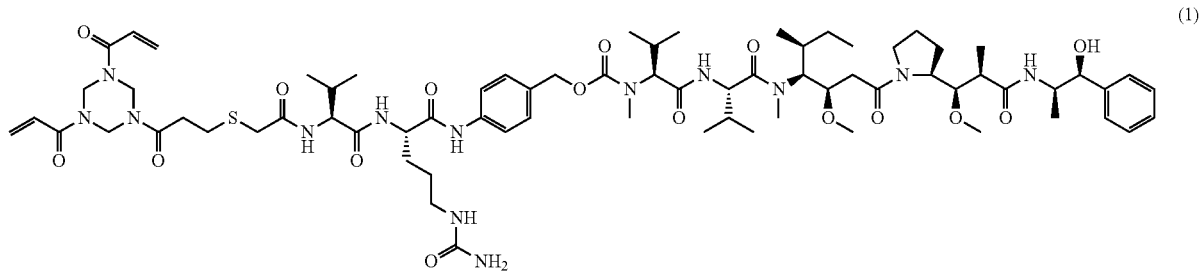

Py-MAA-Val-Cit-PAB-MMAE (2)

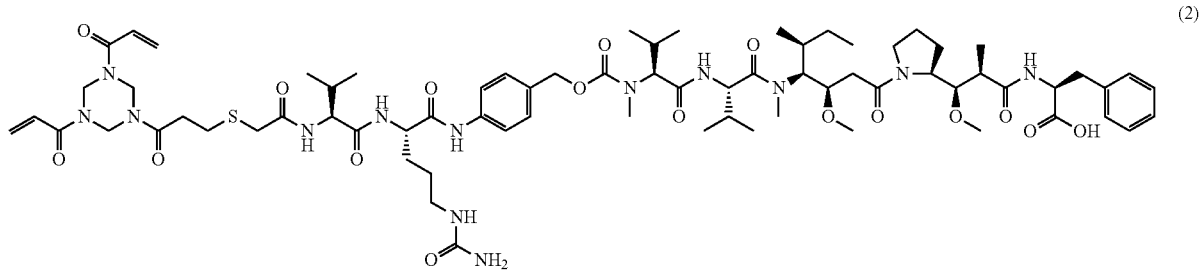

Py-MAA-Val-Cit-PAB-MMAF

-continued
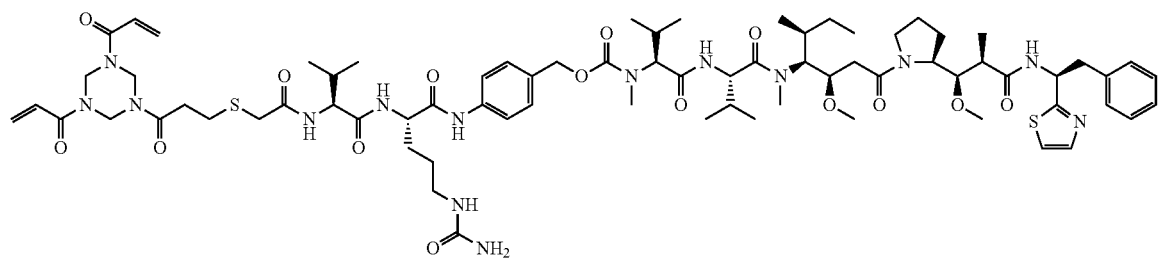
Py-MAA-Val-Cit-PAB-MMAD
(3)
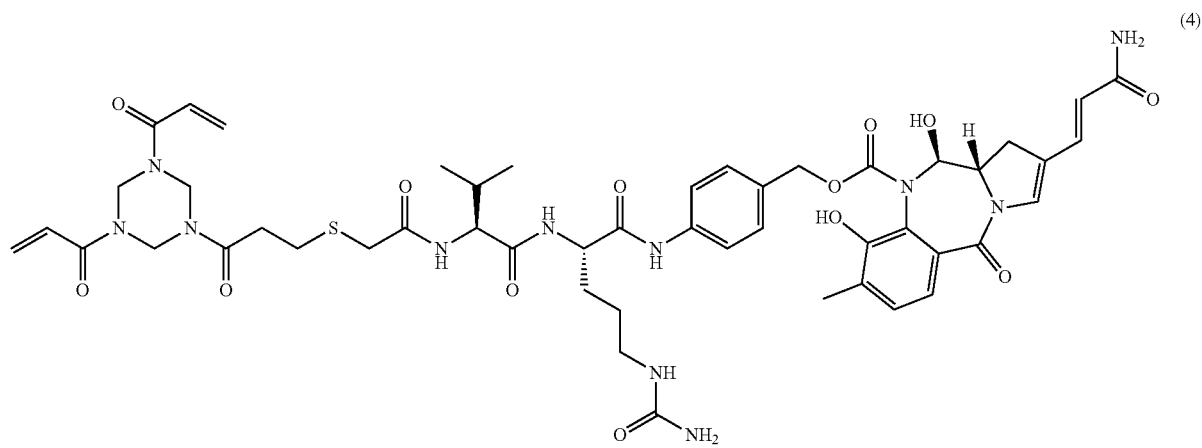
Py-MAA-Val-Cit-PAB-anthramycin
(4)
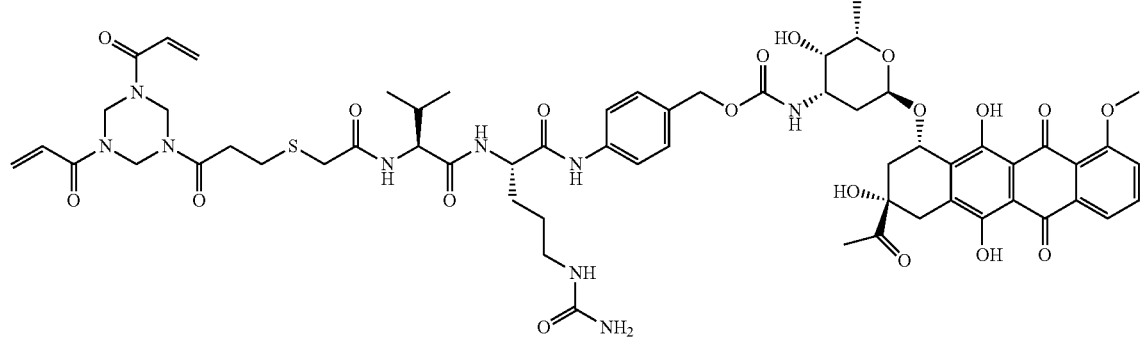
Py-MAA-Val-Cit-PAB-daunorubicin
(5)
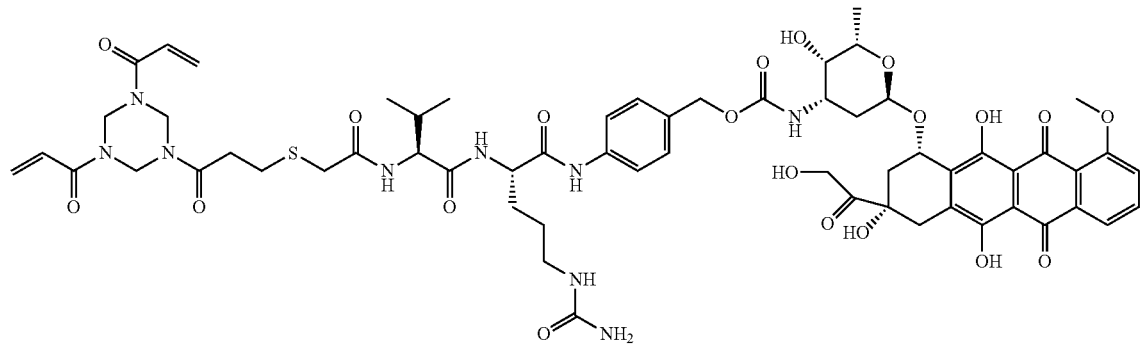
Py-MAA-Val-Cit-PAB-doxorubicin
(6)

(7)
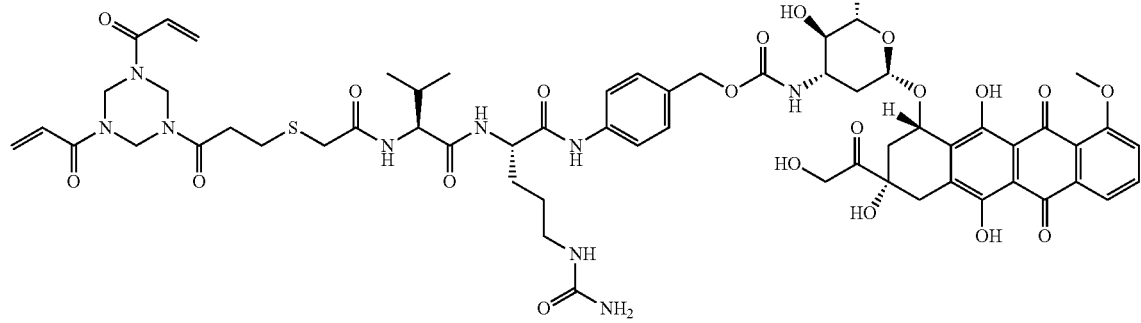
Py-MAA-Val-Cit-PAB-epirubicin
(8)
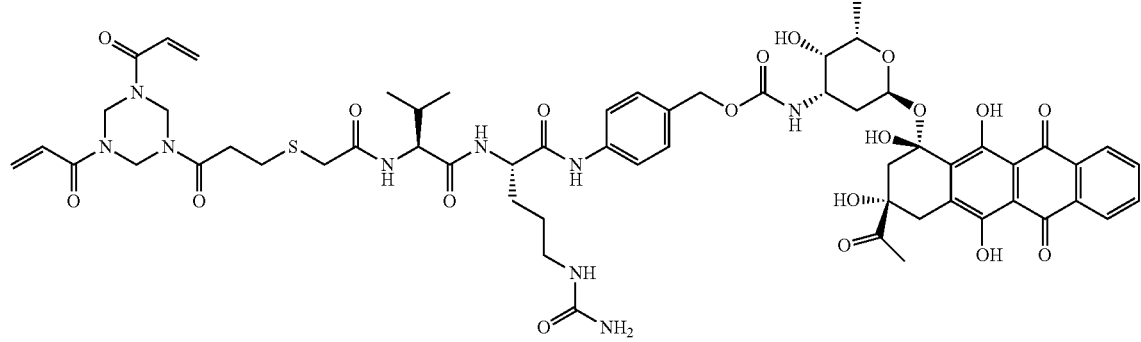
Py-MAA-Val-Cit-PAB-idarubicin
(9)
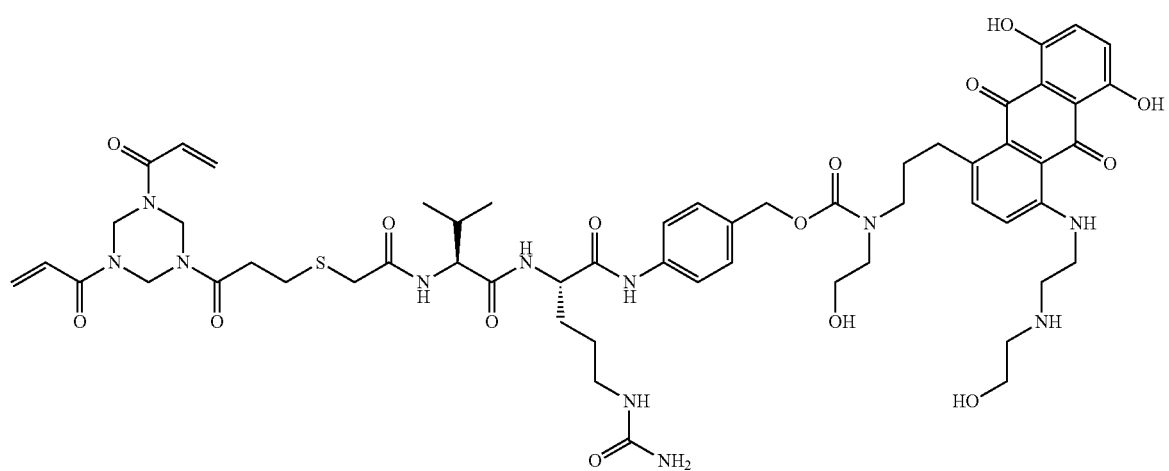
Py-MAA-Val-Cit-PAB-mitoxantrone -continued
(10)
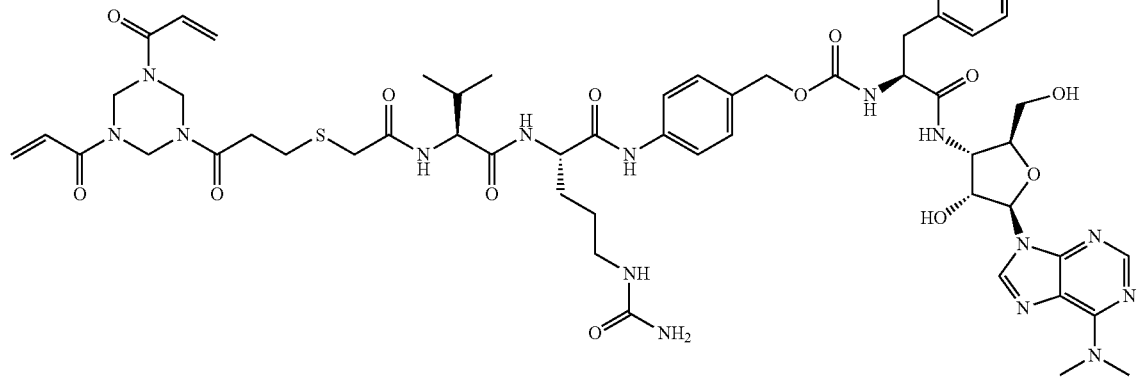
Py-MAA-Val-Cit-PAB-puromycin
(11)
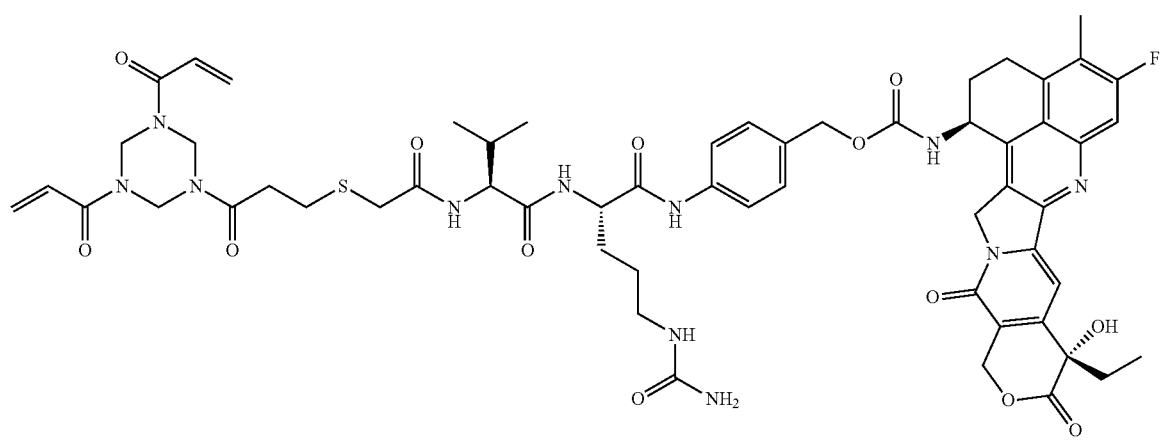
Py-MAA-Val-Cit-PAB-DX8951
(12)
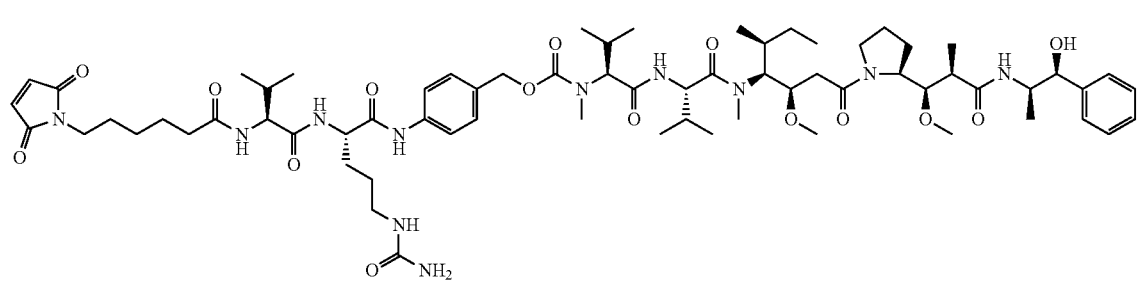
MC-Val-Cit-PAB-MMAE
(13)
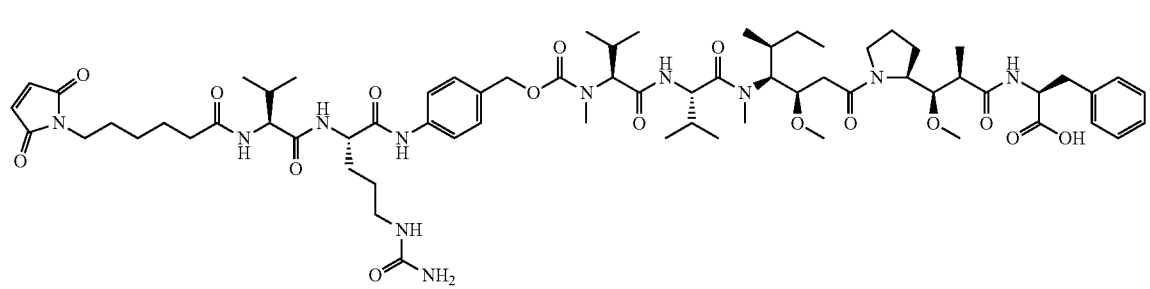
MC-Val-Cit-PAB-MMAF

(14)
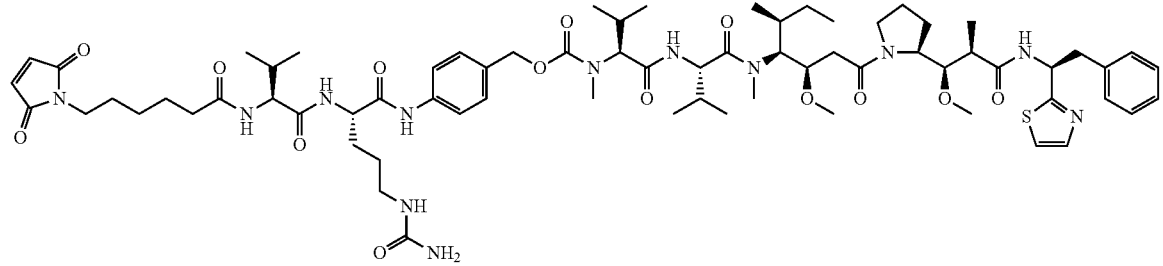
MC-Val-Cit-PAB-MMAD
(15)
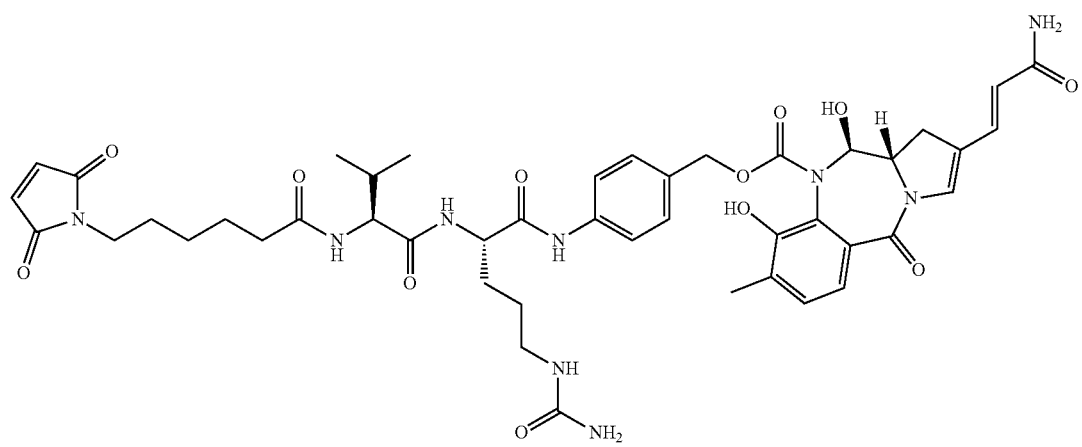
MC-Val-Cit-PAB-anthramycin
(16)
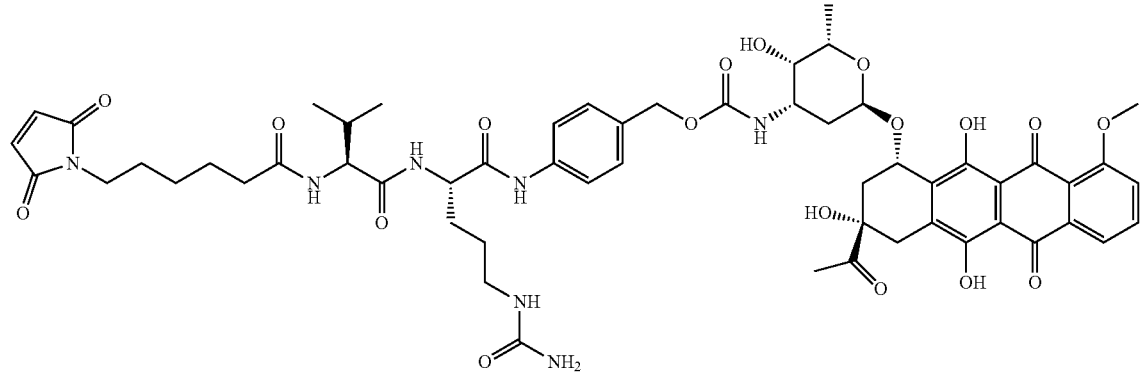
MC-Val-Cit-PAB-daunorubicin

(17)
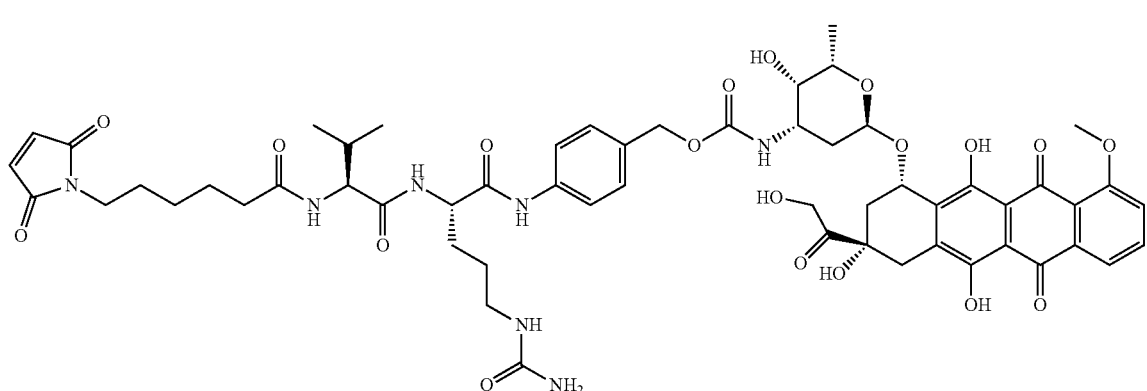
MC-Val-Cit-PAB-doxorubicin
(18)
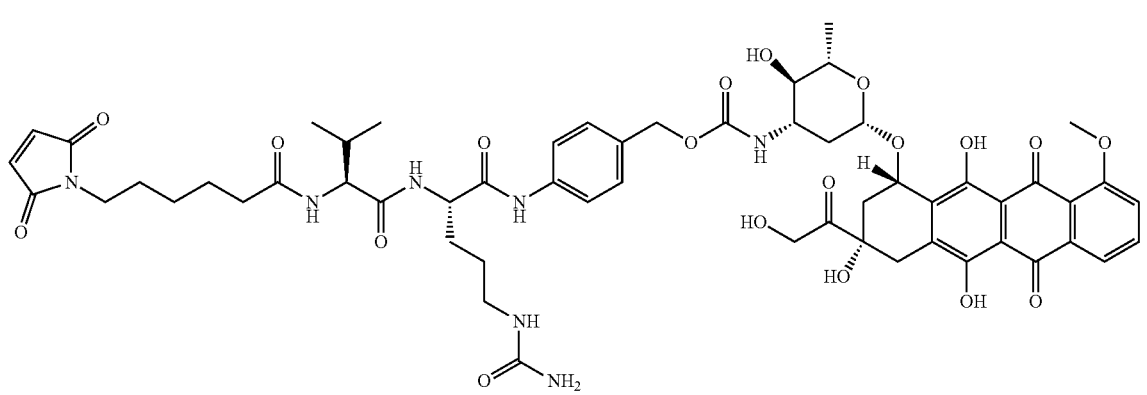
MC-Val-Cit-PAB-epirubicin
(19)
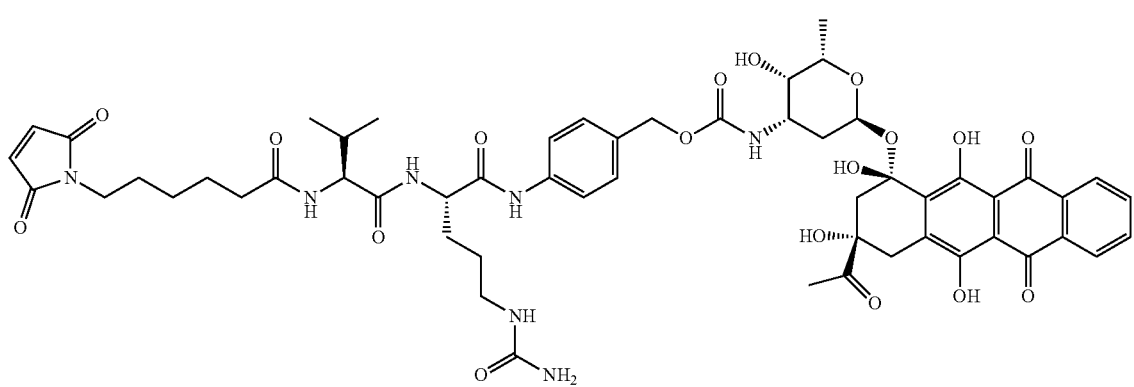
MC-Val-Cit-PAB-idarubicin -continued
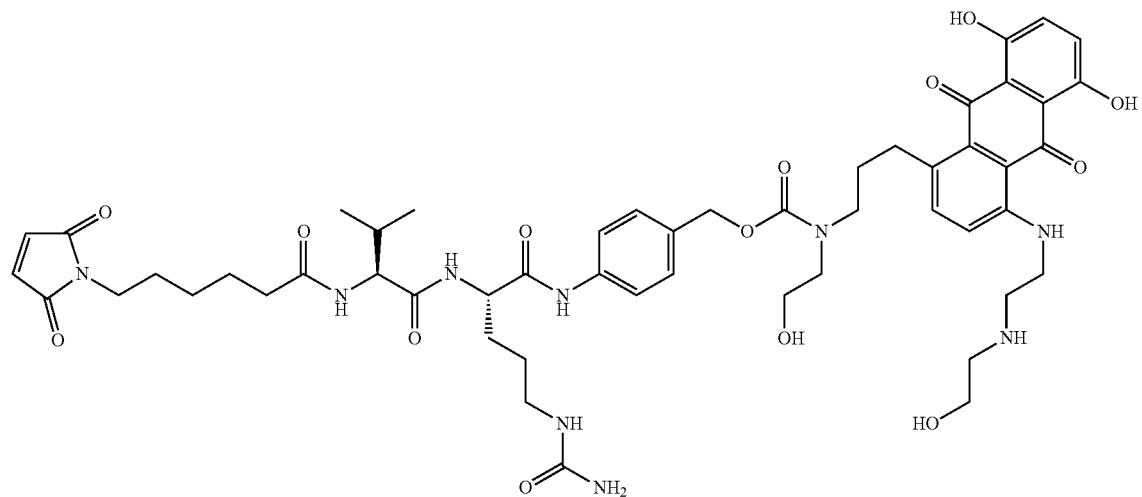
MC-Val-Cit-PAB-mitoxantrone (20)
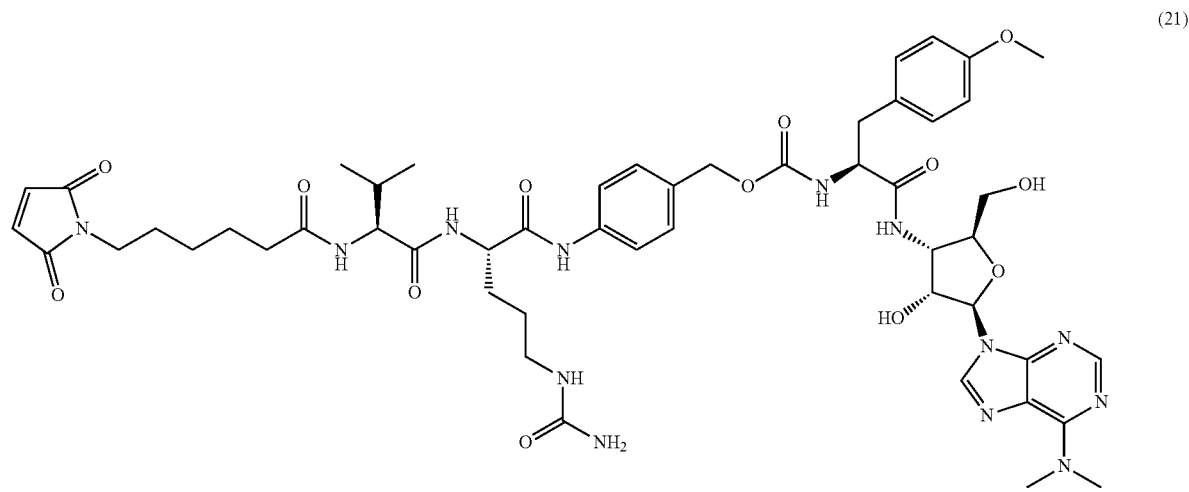
MC-Val-Cit-PAB-puromycin (21)
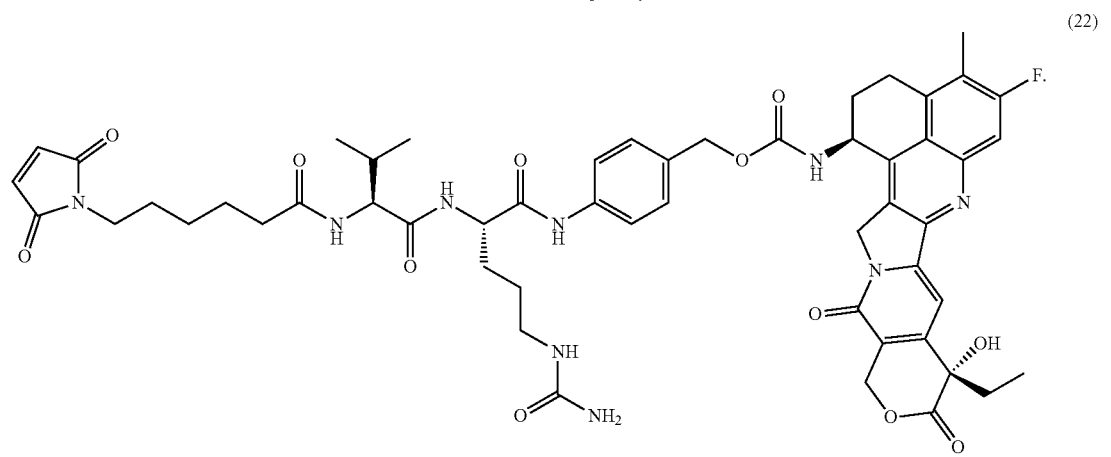
MC-Val-Cit-PAB-DX8951 (22)
\* \* \* \* \*